United States Patent
Zhao et al.

(10) Patent No.: US 11,474,101 B2
(45) Date of Patent: Oct. 18, 2022

(54) DIRECT IMMUNOHISTOCHEMISTRY ASSAY

(71) Applicant: NOVODIAX, INC., Hayward, CA (US)

(72) Inventors: Song Qing Zhao, Madison, WI (US); Jianfu Jeffrey Wang, Union City, CA (US); Jin V. Wu, Union City, CA (US); Zhiqing Zhang, Union City, CA (US)

(73) Assignee: NOVODIAX, INC., Hayward, CA (US)

( * ) Notice: Subject to any disclaimer, the term of this patent is extended or adjusted under 35 U.S.C. 154(b) by 552 days.

(21) Appl. No.: 15/309,405

(22) PCT Filed: May 7, 2015

(86) PCT No.: PCT/US2015/029762
§ 371 (c)(1),
(2) Date: Nov. 7, 2016

(87) PCT Pub. No.: WO2015/171938
PCT Pub. Date: Nov. 12, 2015

(65) Prior Publication Data
US 2017/0074867 A1 Mar. 16, 2017

Related U.S. Application Data

(60) Provisional application No. 61/990,111, filed on May 8, 2014.

(51) Int. Cl.
G01N 33/535 (2006.01)
G01N 33/58 (2006.01)
C07K 16/28 (2006.01)
C07K 16/18 (2006.01)
C07K 16/30 (2006.01)

(52) U.S. Cl.
CPC .......... *G01N 33/535* (2013.01); *C07K 16/18* (2013.01); *C07K 16/2803* (2013.01); *C07K 16/289* (2013.01); *C07K 16/3053* (2013.01); *C07K 2317/21* (2013.01); *G01N 33/581* (2013.01); *G01N 2474/20* (2021.08)

(58) Field of Classification Search
None
See application file for complete search history.

(56) References Cited

U.S. PATENT DOCUMENTS

| | | |
|---|---|---|
| 3,817,837 A | 6/1974 | Rubenstein |
| 3,850,752 A | 11/1974 | Schuurs |
| 3,939,350 A | 2/1976 | Kronick |
| 3,996,345 A | 12/1976 | Ullman |
| 4,275,149 A | 6/1981 | Litman |
| 4,277,437 A | 7/1981 | Maggio |
| 4,366,241 A | 12/1982 | Tom |
| 4,472,509 A | 9/1984 | Gansow |
| 4,657,853 A | 4/1987 | Freytag |
| 4,687,732 A | 8/1987 | Ward |
| 4,737,456 A | 4/1988 | Weng |
| 4,938,948 A | 7/1990 | Ring |
| 5,057,313 A * | 10/1991 | Shih .............. A61K 49/085 424/1.53 |
| 5,196,066 A | 3/1993 | Kusuda |
| 5,229,275 A | 7/1993 | Goroff |
| 5,567,610 A | 10/1996 | Borrebaeck |
| 5,571,894 A | 11/1996 | Wels |
| 5,587,458 A | 12/1996 | King |
| 5,869,046 A | 2/1999 | Presta |
| 6,248,516 B1 | 6/2001 | Winter |
| 6,613,564 B2 * | 9/2003 | Ohbayashi ........ G01N 33/535 435/345 |
| 2004/0265840 A1 * | 12/2004 | Kunitake ............. G01N 1/30 435/6.14 |
| 2005/0026196 A1 * | 2/2005 | Saad .................. C12Q 1/6886 435/6.14 |
| 2006/0246523 A1 * | 11/2006 | Bieniarz ............. C12N 9/0065 435/7.92 |
| 2006/0246524 A1 * | 11/2006 | Bauer ................ A61K 49/0058 435/7.92 |
| 2007/0292887 A1 * | 12/2007 | Taylor ............. G01N 33/57484 435/7.1 |
| 2008/0026366 A1 * | 1/2008 | Harkins ................ G01N 1/30 435/5 |

(Continued)

FOREIGN PATENT DOCUMENTS

| CN | 1196733 A | 10/1998 |
|---|---|---|
| CN | 1300942 A | 6/2001 |

(Continued)

OTHER PUBLICATIONS

Solulink®, RapidDirect® Primary Antibody polyHRP Labeling Kit, (Jul. 2011), available online https://www.interchim.fr/ft/1/116151.pdf [Accessed Sep. 8, 2020] (Year: 2011).*
Barok, M. et al. (Apr. 21, 2011). "Trastuzumab-Dm1 Causes Tumour Growth Inhibition by Mitotic Catastrophe in Trastuzumab-Resistant Breast Cancer Cells In Vivo," Breast Cancer Research 13(2):R46, pp. 1-11.
Baskar, S. et al. (Jan. 15, 2008). "Unique Cell Surface Expression of Receptor Tyrosine Kinase ROR1 in Human B-Cell Chronic Lymphocytic Leukemia," Clin Cancer Res 14(2):396-404.
Battifora, H. et al. (Aug. 1986). "The Influence of Protease Digestion and Duration of Fixation on the Immunostaining of Keratins. A Comparison of Formalin and Ethanol Fixation," J. Histochem. Cytochem. 34(8):1095-1100.

(Continued)

*Primary Examiner* — Ellen J Marcsisin

(74) *Attorney, Agent, or Firm* — Ping Wang; Rimon Law

(57) ABSTRACT

The application is to antibodies which have been labelled with polyenzymes (multiple enzymes), specifically polyperoxidases, for use in direct immunohistochemical assays of tissues. The antibodies used diagnostically may also be antibodies which are used therapeutically.

19 Claims, 16 Drawing Sheets

(56) References Cited

U.S. PATENT DOCUMENTS

| | | | |
|---|---|---|---|
| 2010/0035246 A1* | 2/2010 | Lushi | C12Q 1/6879 |
| | | | 435/6.11 |
| 2010/0151460 A1* | 6/2010 | Winther | G01N 33/6803 |
| | | | 435/6.16 |
| 2010/0247536 A1* | 9/2010 | Olle | C07K 16/30 |
| | | | 424/134.1 |
| 2012/0112098 A1* | 5/2012 | Hoyt | G01N 21/6458 |
| | | | 250/459.1 |
| 2013/0017195 A1* | 1/2013 | O'Shannessy | C07K 16/28 |
| | | | 424/133.1 |

FOREIGN PATENT DOCUMENTS

| | | |
|---|---|---|
| CN | 1945333 A | 4/2007 |
| CN | 101535244 A | 9/2009 |
| CN | 102590512 A | 7/2012 |
| EP | 0175560 A2 | 3/1986 |
| EP | 0404097 A2 | 12/1990 |
| EP | 0404097 A3 | 10/1991 |
| EP | 0404097 B1 | 9/1996 |
| EP | 0842948 A1 | 5/1998 |
| EP | 1111385 A2 | 6/2001 |
| FR | 2734365 A1 | 11/1996 |
| JP | S60501573 A | 9/1985 |
| JP | H09511067 A | 11/1997 |
| JP | 2001181299 A | 7/2001 |
| JP | 3925663 B2 | 3/2007 |
| JP | 2007513334 A | 5/2007 |
| WO | WO199301161 A1 | 1/1993 |
| WO | WO199316185 A2 | 8/1993 |
| WO | WO199316185 A3 | 9/1993 |
| WO | WO2003104424 A2 | 12/2003 |
| WO | 2005054860 A1 | 6/2005 |
| WO | WO2010078376 A2 | 7/2010 |

OTHER PUBLICATIONS

Chothia, C. et al. (1987). "Canonical Structures for the Hypervariable Regions of Immunoglobulins," J. Mol. Biol, 196:901-917.

Christian, S. et al. (2003; e-pub. Nov. 24, 2003). "Nucleolin Expressed at the Cell Surface is a Marker of Endothelial Cells in Angiogenic Blood Vessels," J Cell Biol. 163(4):871-878.

Dhawan, S. (2002). "Design and Construction of Novel Molecular Conjugates for Signal Amplification (I): Conjugation of Multiple Horseradish Peroxidase Molecules to Immunoglobulin Via Primary Amines on Lysine Peptide Chains," Peptides 23:2091-2098.

Dhawan, S. (2006). "Signal Amplification Systems in Immunoassays: Implications For Clinical Diagnostics," Expert Review of Molecular Diagnostics 6(5):749-760.

European Supplementary Search Report dated Feb. 19, 2018 for European Patent Application No. 15788690.4 filed on Nov. 24, 2016, eleven pages.

Frolova, I.I. et al. (2004). "Clinical-Morphological Investigations of Cervical Dyskeratosis and Cervical Intraepithelial Neoplasia," RUDN newspaper, Medicine N series (Вестник РУДН, серия Медицина N) 1(25):79-85.(English Introduction only).

Hofman, F.M. et al. (2013; e-published on Nov. 2013). "Immunohistochemistry," in Current Protocols in Immunology, John Wiley & Sons, Inc., Hoboken, NJ, USA, pp. 21.4.1-21.4.26.

Holliger, P. et al. (Jul. 1993). ""Diabodies": Small Bivalent and Bispecific Antibody Fragments," Proceedings of the National Academy of Sciences 90:6444-6448.

Hudson, P.J. et al. (Jan. 2003). "Engineered Antibodies," Nature Medicine 9(1):129-134.

International Preliminary Report On Patentability dated Nov. 8, 2016, for PCT Application No. PCT/US2015/029762, internationally filed on May 7, 2015, 6 pages.

International Search Report dated Jul. 16, 2015, for PCT Application No. PCT/US2015/029762, internationally filed on May 7, 2015, 6 pages.

Johnson, K.S. et al. (1993). "Human Antibody Engineering," Current Opinion in Structural Biology 3:564-571.

Leong, A.S.-Y. et al. (1996). "Epitope Retrieval with Microwaves. A Comparison of Citrate Buffer and EDTA with Three Commercial Retrieval Solutions," Applied Immunohistochemistry 4(3):201-207.

Liu, R. et al. (Jan. 2008; e-pub. Jan. 19, 2008). "Phosphorylated PP2A (tyrosine 307) is Associated with Alzheimer Neurofibrillary Pathology," J. Cell Mol. Med. 12(1):241-257.

Lonberg, N. et al. (Apr. 28, 1994). "Antigen-Specific Human Antibodies From Mice Comprising Four Distinct Genetic Modifications," Nature 368(6474):856-859.

McCafferty, J. et al. (Dec. 6, 1990). "Phage Antibodies: Filamentous Phage Displaying Antibody Variable Domains," Nature 348:552-554.

Pluckthun, A. (1994). "Antibodies from *Escherichia coli*," Chapter 11 in The Pharmacology of Monoclonal Antibodies, Rosenburg and Moore eds., Springer-Verlag, New York, 113:269-315.

Porkka, K. et al. (May 28, 2002). "A Fragment of the HMGN2 Protein Homes to the Nuclei of Tumor Cells and Tumor Endothelial Cells in Vivo," Proc Natl Acad Sci, USA 99(11):7444-7449.

Solulink. (Jul. 2011). "RapidDirect Primary Antibody PolyHRP Labeling Kit," Cat. No. A-9402-001, located at URL: http://www.interchim.fr/ft/1/116151.pdf, last visited on Jan. 17, 2018, 12 pages.

Taylor, L.D. et al. (Apr. 1994). "Human Immunoglobulin Transgenes Undergo Rearrangement, Somatic Mutation and Class Switching in Mice That Lack Endogenous IgM," International Immunology 6(4):579-591.

Tse, J et al. (Dec. 1988). "Immunohistochemical Demonstration of Estrophilin in Mouse Tissues Using a Biotinylated Monoclonal Antibody," Journal of Histochemistry and Cytochemistry 36(12):1527-1531.

Wallkamm, V. et al. (Oct. 14, 2014). "Live Imaging of Xwnt5A-ROR2 Complexes," Plos One 9(10):e109428, pp. 1-9.

Written Opinion dated Jul. 16, 2015, for PCT Application No. PCT/US2015/029762, internationally filed on May 7, 2015, 5 pages.

Chen, S. et al. (2017). "Rapid and Sensitive Multiplexing Approach with Novodiax IhcDirectTMTechnology," Poster, presented at Molecular Med Tri-con, San Francisco, CA, 2 pages.

Cheraghi, N. et al. (2018). "Melanoma Treated with Mohs Micrographic Surgery Using a Modified 15-minute Mart-1 Immunostain: Discussion on Technique and Experience," Poster, presented at American College of Mohs Surgery, Chicago, IL, May 6, 2018, 3 pages.

Glinert, R. et al. (May 2017). "Use of Ultra-fast One-step CK5 IHC for Identifying BCC and SCC During Mohs Surgery," Journal of Investigative Dermatology 137(Supplement 1), 22 pages, Abstract No. 268.

Liu, H. et al. (2016). "Optimization of Rapid Immunohistochemical Stains on Frozen Tissue Sections," Poster, presented at USCAP Annual Meeting, Seattle, WA, Mar. 12-18, 2016, 2 pages.

Liu, M. et al. (Jul. 2019). "A Direct Immunohistochemistry (IHC) Method Improves the Intraoperative Diagnosis of Breast Papillary Lesions Including Breast Cancer," Discover Medicine 28:29-37.

Mei, L. et al. (2018). "Application of Rapid Direct Immunohistochemistry for Intraoperative Diagnosis of Breast Lesions and Sentinel Node Biopsies," Chinese Journal of Diagnostic Pathology 25(03):170-176, (English Abstract only).

Nakane, P.K. et al. (1967). "Enzyme-Labeled Antibodies: Preparation and Application for the Localization of Antigens," The Journal of Histochemistry and Cytochemistry 14(12):929-931.

Wang, L. et al. (2015). "Direct IHC by Using PolyHRP Labeled Trastuzumab (Herceptin)-a Potential New Companion Diagnostic Test for Herceptin Treatment," Poster, presented at World CDx Conference, Boston, MA, 1 page.

Wang, L. et al. (2016). "Use of Herceptin Based IHC as a Potential CDx for Herceptin Treatment," Poster, presented at USCAP Annual Meeting, Seattle, WA, Mar. 12-18, 2016, 2 pages.

Xin, S. et al. (2017). "Application of Rapid Direct Immunohistochemistry for Intraoperative Diagnosis of Breast Papillary Lesions," Chinese Journal of Diagnostic Pathology 24(10):768-773, (English Abstract only).

(56) References Cited

OTHER PUBLICATIONS

Zhang, Y. et al. (2016). "Development of a Practical 10-min Intraoperative IHC Product Line," Poster, presented at ISNS 2016 Biannual meeting, Italy, 3 pages.

* cited by examiner

A

B

A

B

A

B

A

B

A

B

A

B

E

F

G

H

DIRECT IMMUNOHISTOCHEMISTRY ASSAY

CROSS-REFERENCE TO RELATED APPLICATION

This application is a National Phase application under 35 U.S.C. § 371 of International Application No. PCT/US2015/029762, filed May 7, 2015, which claims priority from U.S. Provisional Ser. No. 61/990,111, filed on May 8, 2014, titled RAPID IMMUNOHISTOCHEMISTRY ASSAY, the disclosure of each which is hereby incorporated by reference in its entirety for all purposes.

FIELD OF THE INVENTION

The present invention relates to compositions, methods, and kits for direct immunohistochemical staining of tissue and uses thereof.

BACKGROUND OF THE INVENTION

Frequently during surgery, tissue biopsy samples may be removed from a patient and sent from the operating room to a pathology laboratory for analysis, for example, by frozen tissue section diagnosis. Methodology for frozen tissue section diagnosis may consist of freezing tissue in a pathology lab, sectioning the frozen tissue, and performing standard Hematoxylin and Eosin (H/E) staining. H/E staining is a general-purpose technique used to help a medical pathologist diagnose tissue pathologies. However, H/E staining has a number of limitations including, for example, that it non-specifically stains tissue and also may not identify specific proteins in tissue. Identification of specific proteins in tissue, for example by using a procedure sometimes referred to as immunohistochemistry (IHC), may help a pathologist intraoperatively diagnose numerous tissue pathologies. Examples may include sentinel lymph node biopsies (for potential metastatic carcinomas and melanomas), undifferentiated tumors (potential carcinomas, lymphomas, and melanomas), and biopsies of margins (looking at the edges of excised tissue to see if the entire tumor has been removed).

Immunohistochemical staining of tissue sections is a reliable method of assessing the presence, or lack thereof, and alteration of proteins in a heterogeneous tissue. Generally, IHC techniques utilize an antibody to probe and visualize cellular antigens in situ. Due to the often diffuse distribution of proteins in tissue, signal amplification is needed to visualize cellular antigens. Techniques for signal amplification include, for example, use of a secondary antibody that binds to the primary antibody specific to the cellular antigen and biotin-avidin systems. Chromagenic or fluorescent moieties on the secondary antibody or biotin-avidin signal amplification system are used to detect the presence of the cellular antigen. The IHC technique excels because it avoids the unwanted effects of disaggregation and allows for evaluation of individual cells in the context of morphology. Moreover, the target protein is not altered by the freezing process and thus IHC has potential as a tool for intraoperative pathological analysis of resected tissue.

However, current IHC techniques may require 60 to 120 minutes to obtain results. Intraoperative guidelines, such as those provided by the College of American Pathologists, typically recommend reporting pathology data to the surgeon within approximately 20 minutes. Thus, current IHC techniques are too time intensive to be useful as an intraoperative tool. Furthermore, current IHC techniques can harbor artifacts caused by the signal amplification technique used, for example, non-specific binding of the secondary antibody or the presence of endogenous biotin. Therefore, there is a need for improved IHC techniques.

IHC techniques are also useful for retrospective analysis of tissue. Most pathological samples are not prepared as frozen tissues, but are formalin-fixed and paraffin-embedded (FFPE) to allow for archival storage and histological analysis at a later time. Because paraffin-embedded samples are widely available for retrospective studies, rapid and reliable methods are needed for the quantitative detection of proteins from such samples.

Compositions and methods for the quantification of protein from frozen and paraffin-embedded tissues are particularly needed for the study of protein expression in tumor tissues. For example, expression levels of certain receptors or enzymes can indicate the likelihood of success of a particular treatment. Thus, there is also a need in the art for sensitive and quantitative IHC methods capable of rapidly detecting an antigen, such as a tumor antigen.

SUMMARY OF THE INVENTION

Provided herein are methods, compositions, and kits for detecting the presence or absence of a target analyte in a tissue sample.

Provided herein are methods for detecting a target analyte in a tissue, comprising:

contacting the tissue comprising the target analyte with polymeric-enzyme/antibody conjugates comprising a polymeric-enzyme/antibody conjugate comprising a plurality of enzyme molecules and an antibody recognizing the target analyte to form a complex comprising the target analyte and the polymeric-enzyme/antibody conjugate; substantially removing the polymeric-enzyme/antibody conjugates that do not form the complex; and contacting the tissue with a substrate of the plurality of enzyme molecules, thereby detecting the target analyte. In some embodiments, the tissue is frozen tissue.

In some embodiments according to (or as applied to) any of the embodiments above, the method further comprises a blocking step prior to the step of contacting the tissue comprising the target analyte with polymeric-enzyme/antibody conjugates comprising a polymeric-enzyme/antibody conjugate comprising a plurality of enzyme molecules and an antibody recognizing the target analyte to form a complex comprising the target analyte and the polymeric-enzyme/antibody conjugate, wherein the blocking step comprises contacting the tissue with a blocking agent. In some embodiments, the tissue is frozen tissue. In some embodiments, the blocking agent comprises skim milk, BSA, cold fish skin gelatin, casein, or an animal serum.

In some embodiments according to (or as applied to) any of the embodiments above, the tissue is fixed in a fixing solution comprising an aldehyde.

In some embodiments according to (or as applied to) any of the embodiments above, the fixing solution comprises formalin.

In some embodiments according to (or as applied to) any of the embodiments above, the tissue is paraffin-embedded.

In some embodiments according to (or as applied to) any of the embodiments above, the tissue is a tissue section, a clinical smear, or a cultured cell or tissue. In some embodiments, the tissue section is selected from the group consisting of tissue sections of brain, adrenal glands, colon, small intestines, stomach, heart, liver, skin, kidney, lung, pancreas, testis, ovary, prostate, uterus, thyroid, and spleen of a mammal.

In some embodiments according to (or as applied to) any of the embodiments above, the enzyme molecule is selected from the group consisting of: beta-D-galactosidase, glucose oxidase, horseradish peroxidase, alkaline phosphatase, beta-lactamase, glucose-6-phosphate dehydrogenase, urease, uricase, superoxide dismutase, luciferase, pyruvate kinase, lactate dehydrogenase, galactose oxidase, acetylcholinesterase, enterokinase, tyrosinase, and xanthine oxidase.

In some embodiments according to (or as applied to) any of the embodiments above, the polymeric-enzyme/antibody conjugate comprises at least 6 enzyme molecules per polymeric-enzyme/antibody conjugate. In some embodiments, the polymeric-enzyme/antibody conjugate comprises between about 6 and about 80 enzyme molecules per polymeric-enzyme/antibody conjugate.

In some embodiments according to (or as applied to) any of the embodiments above, the step of contacting the tissue comprising the target analyte with polymeric-enzyme/antibody conjugates comprising a polymeric-enzyme/antibody conjugate comprising a plurality of enzyme molecules and an antibody recognizing the target analyte to form a complex comprising the target analyte and the polymeric-enzyme/antibody conjugate is performed at an incubation temperature of between about 15° C. and about 37° C.

In some embodiments according to (or as applied to) any of the embodiments above, the step of contacting the tissue comprising the target analyte with polymeric-enzyme/antibody conjugates comprising a polymeric-enzyme/antibody conjugate comprising a plurality of enzyme molecules and an antibody recognizing the target analyte to form a complex comprising the target analyte and the polymeric-enzyme/antibody conjugate is performed for an incubation period of between about 3 minutes and about 30 minutes. In some embodiments, the incubation period is between about 5 minutes and about 15 minutes.

Provided herein are methods of making a polymeric-enzyme/antibody conjugate, comprising: conjugating a polymeric-enzyme comprising a plurality of enzyme molecules to an antibody. In some embodiments, the antibody is a therapeutic antibody.

Provided herein are methods of treating an individual having a disease with an agent, comprising detecting the presence of a target analyte using a polymeric-enzyme/antibody conjugate comprising a plurality of enzyme molecules conjugated to an antibody recognizing the target analyte according to (or as applied to) any of the embodiments above. In some embodiments, the agent is a therapeutic antibody. In some embodiments, the antibody that specifically binds the target analyte and the therapeutic antibody are the same.

Provided herein are polymeric-enzyme/antibody conjugate comprising a plurality of enzyme molecules and a therapeutic antibody. Also provided are kits comprising the polymeric-enzyme/antibody conjugates according to any of the embodiments above. In some embodiments, the kit further comprises a substrate of the plurality of enzyme molecules. In some embodiments, the kit further comprises instructions for use according to any of the embodiments above.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts results (100×) of direct immunohistochemistry stain of frozen human lymph node tissue. The lymph node contains metastatic breast ductal carcinoma. The metastatic carcinoma cells are stained directly by HRP polymer labeled mouse anti-human lower molecular weight keratin monoclonal antibodies (CK8/18, clone C94); and the incubation time for the direction immunohistochemistry stain was 3 minutes at room temperature. FIG. 1B shows 200× magnification of the tissue. Exemplary stained areas are indicated by an arrow.

FIG. 2A depicts results (100×) of direct immunohistochemistry stain of frozen human lymph node tissue. The lymph node contains metastatic breast ductal carcinoma. The metastatic carcinoma cells are stained directly by Novodiax HRP polymer labeled mouse anti-human lower molecular weight keratin monoclonal antibodies (CK8/18, clone C94); and the incubation time for the direction immunohistochemistry stain was 5 minutes at room temperature. FIG. 2B shows 200× magnification of the tissue. Exemplary stained areas are indicated by an arrow.

FIG. 3A depicts results (100×) of direct immunohistochemistry stain of frozen human lymph node tissue. The lymph node contains metastatic breast ductal carcinoma. The metastatic carcinoma cells are stained directly by HRP polymer labeled mouse anti-human lower molecular weight keratin monoclonal antibodies (CK8/18, clone C94); and the incubation time for the direction immunohistochemistry stain was 8 minutes at room temperature. FIG. 3B shows 200× magnification of the tissue. Exemplary stained areas are indicated by an arrow.

FIG. 4A depicts H/E staining slide of frozen section tissue, 10× magnification. The tissue is an axillary lymph node containing metastatic breast ductal carcinoma. Most lymphoid tissue is replaced by tumor. FIG. 4B depicts H/E staining slide of frozen section tissue, 10× magnification. The tissue is an axillary lymph node containing metastatic breast ductal carcinoma. Most lymphoid tissue is replaced by tumor.

FIG. 8A depicts results (20×) of direct immunohistochemistry stain of formalin fixed human prostatic tissue. The prostatic gland epithelial cells are stained directly by Novodiax HRP polymer labeled mouse anti-human lower molecular weight keratin monoclonal antibodies (CK8/18, clone C94); and the incubation time for the direction immunohistochemistry stain was 3 minutes at 37° C. FIG. 8B depicts results (40×) of direct immunohistochemistry staining of formalin fixed human prostatic tissue. The prostatic gland epithelial cells are stained directly by Novodiax HRP polymer labeled mouse anti-human lower molecular weight keratin monoclonal antibodies (CK8/18, clone C94); and the incubation time for the direction immunohistochemistry stain was 3 minutes at 37° C.

DETAILED DESCRIPTION OF THE INVENTION

Figure 1:
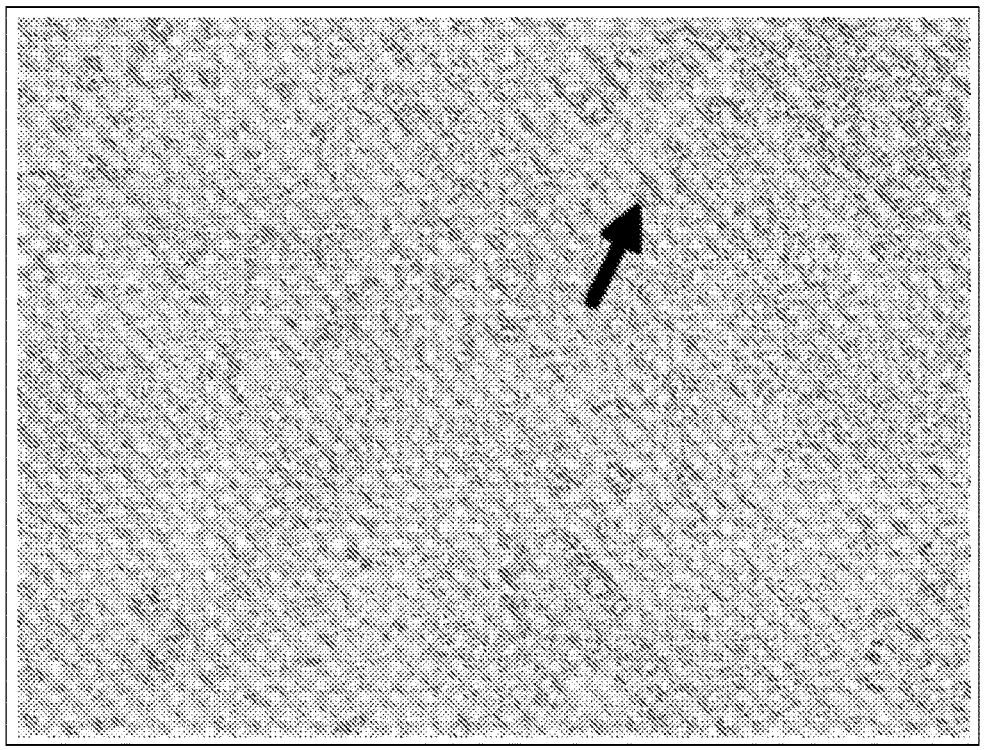
FIG. 1 shows representative images of direct IHC staining of frozen human lymph node tissue using a poly-HRP anti-Ck8/18 antibody conjugate.
Figure 1:
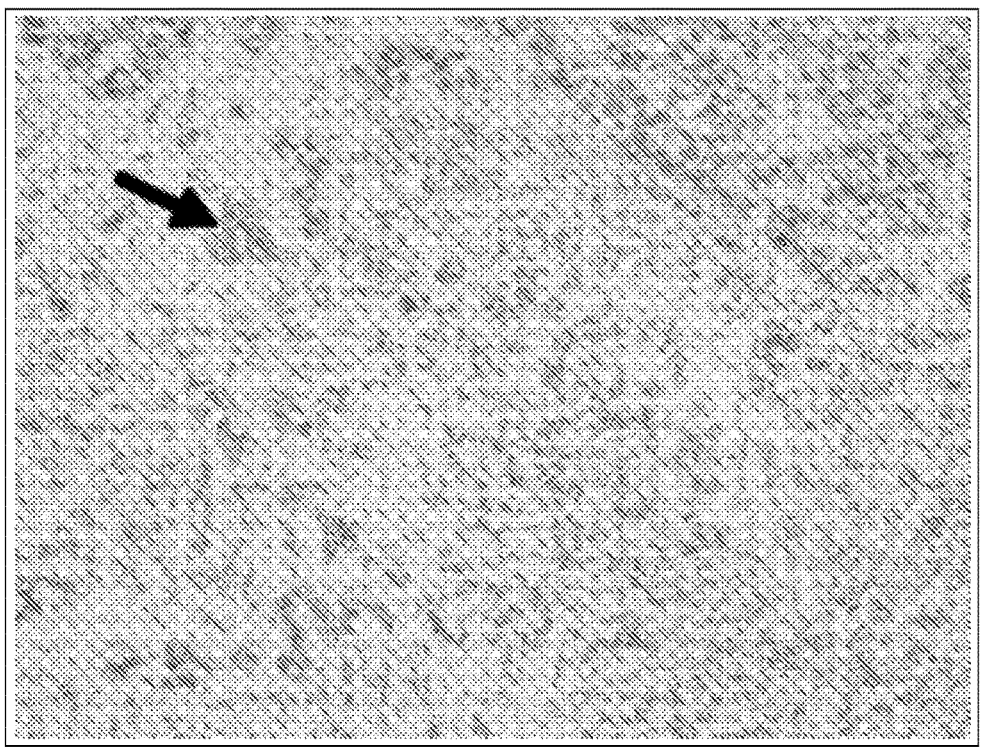
Figure 2:
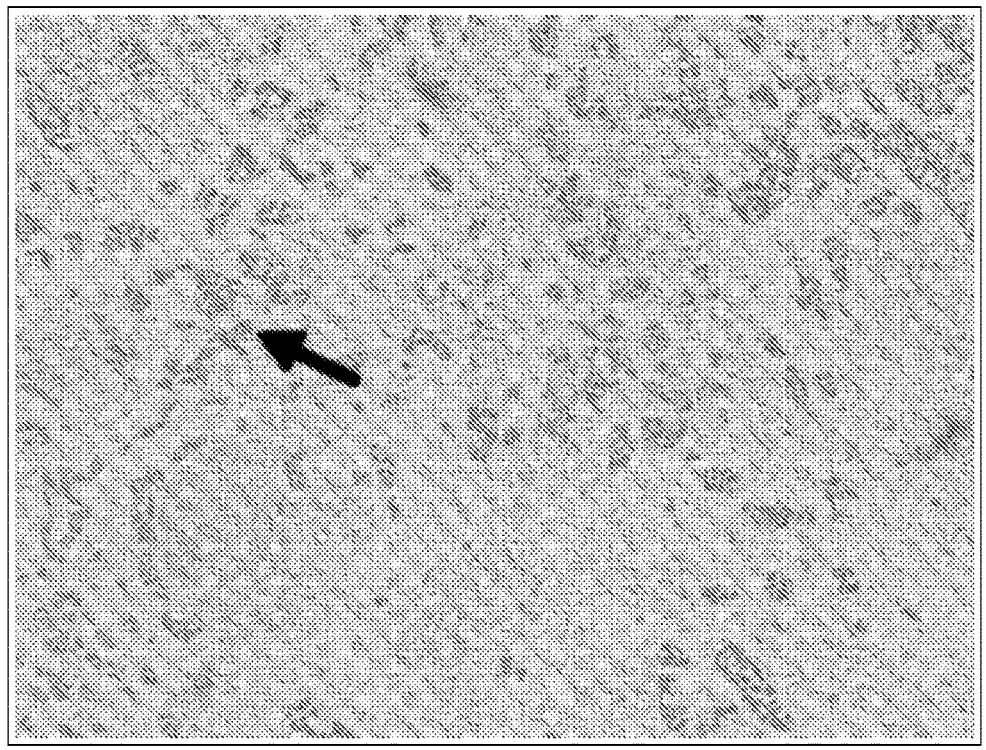
FIG. 2 shows representative images of direct IHC staining of frozen human lymph node tissue using a poly-HRP anti-Ck8/18 antibody conjugate.
Figure 2:
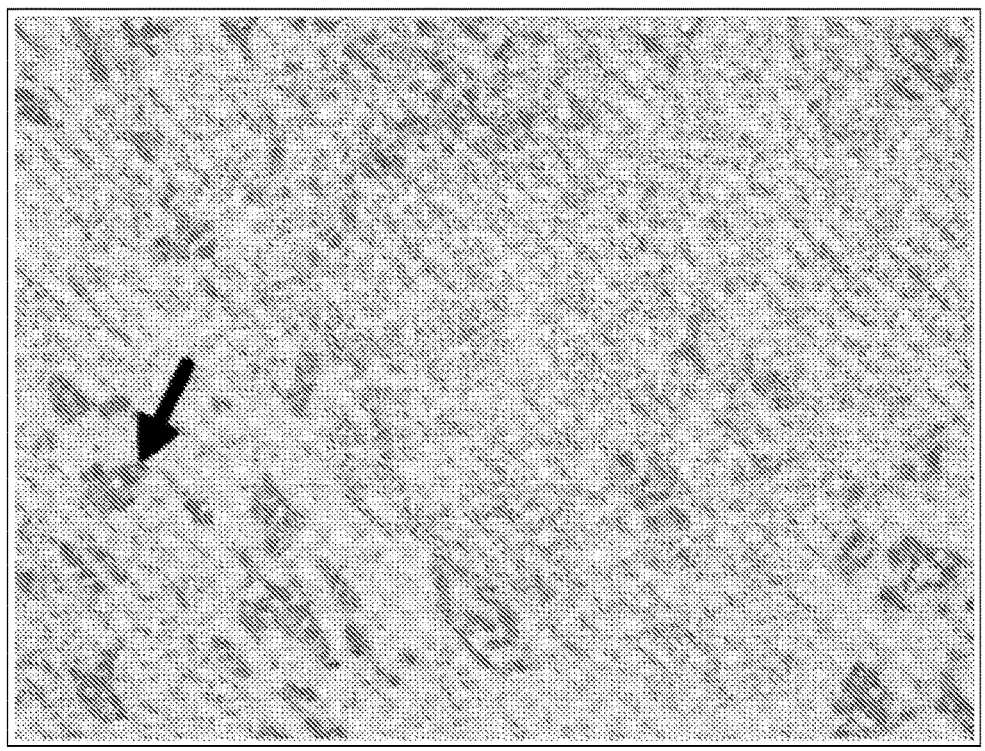
Figure 3:
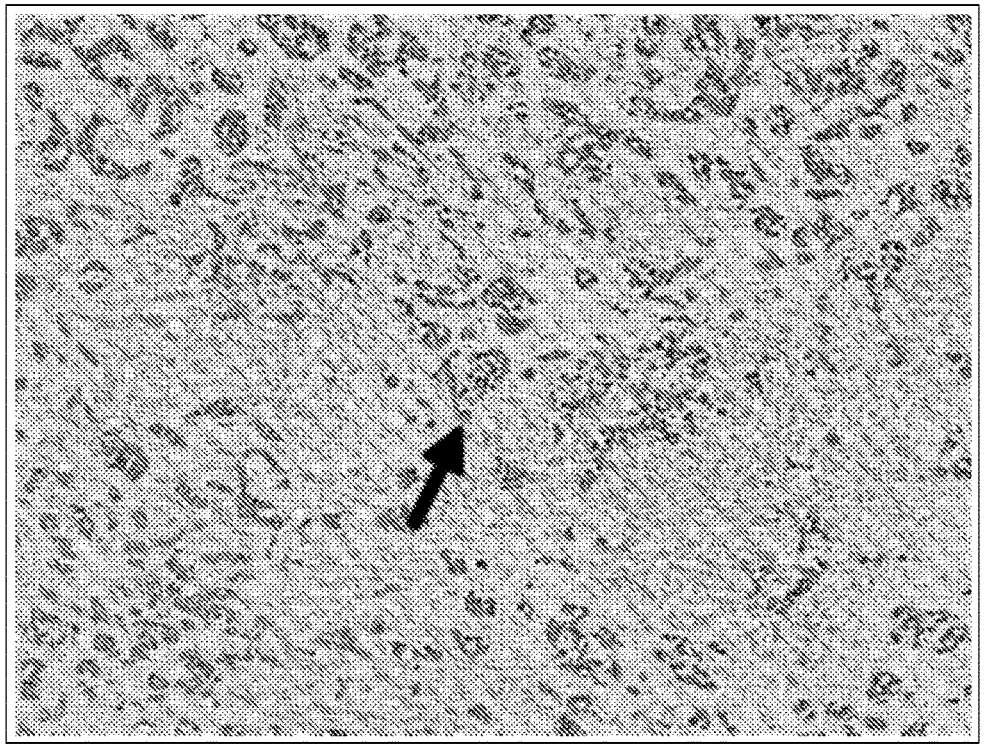
FIG. 3 shows representative images of direct IHC staining of frozen human lymph node tissue using a poly-HRP anti-Ck8/18 antibody conjugate.
Figure 3:
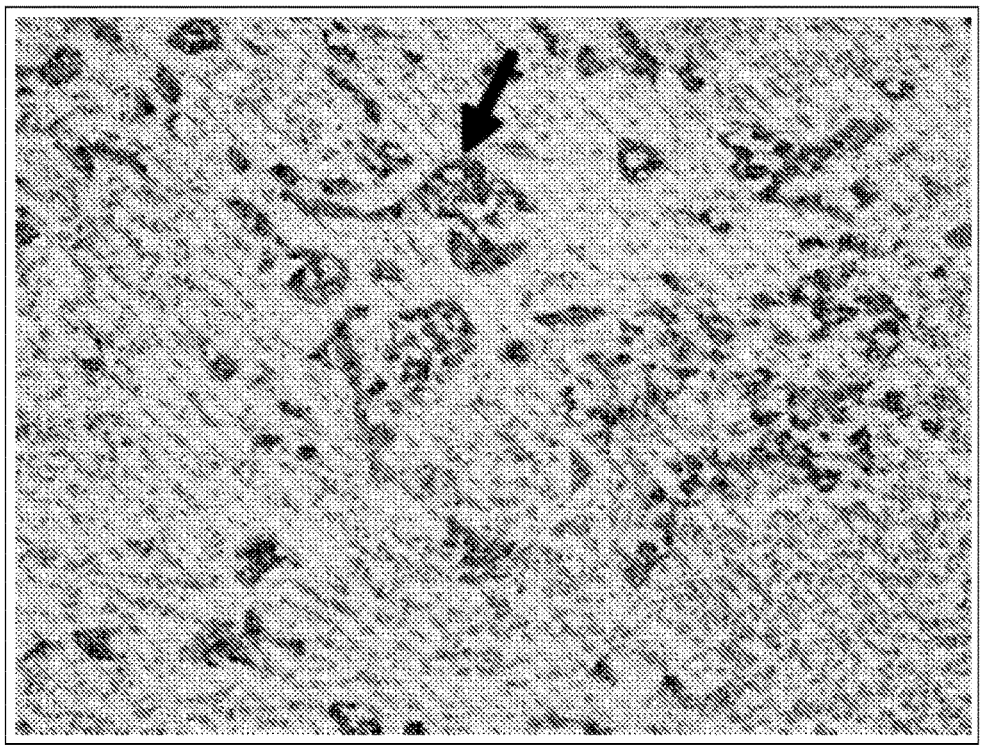
Figure 4:
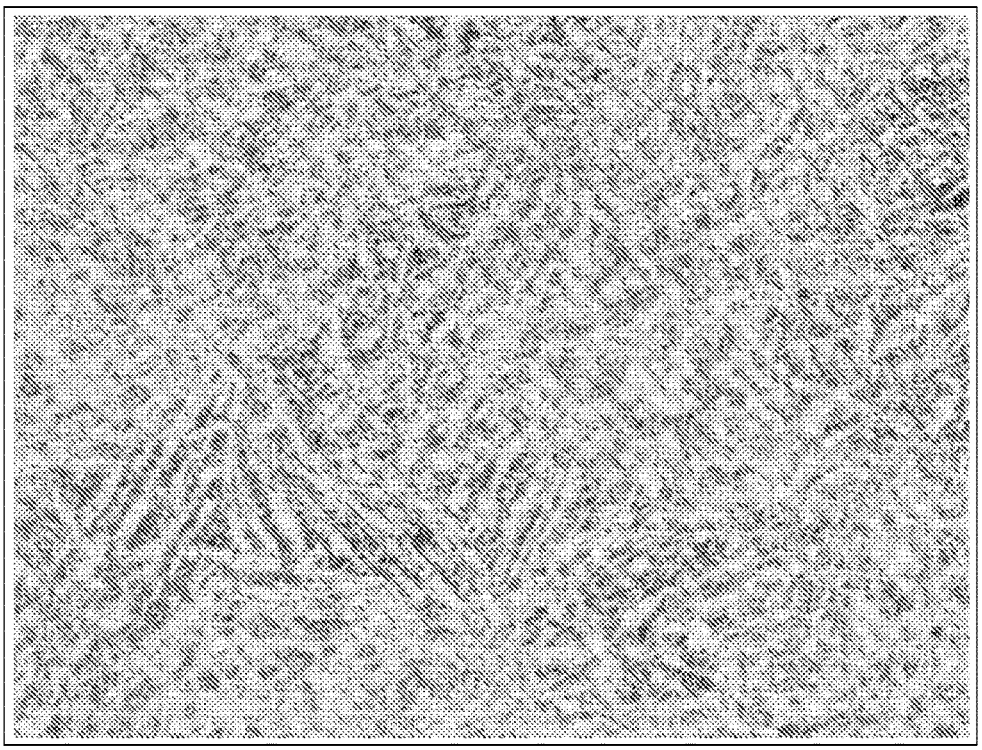
FIG. 4 shows representative images of H/E staining.
Figure 4:
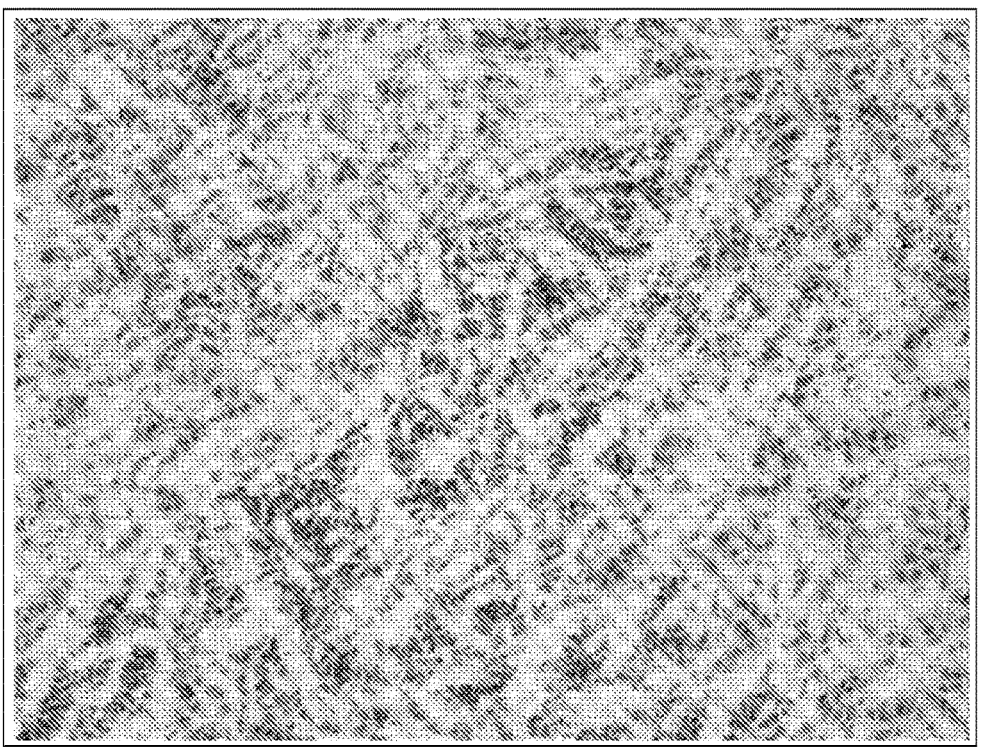
Figure 5:
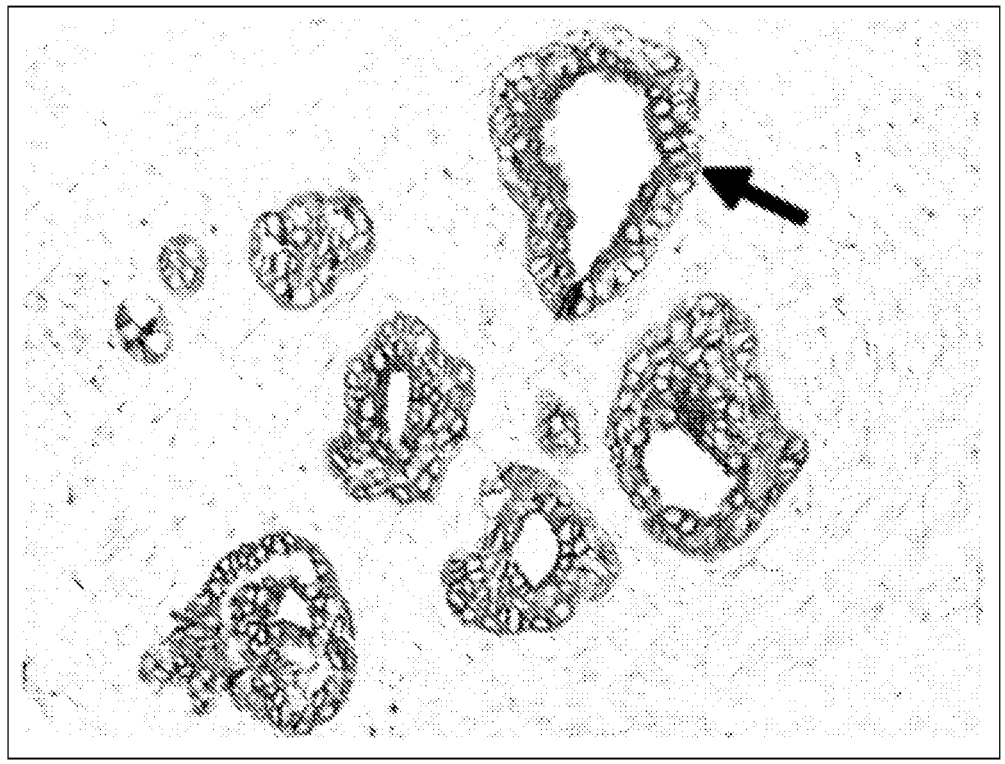
FIG. 5 depicts a representative image of direct IHC staining of a formalin fixed tissue slide using Novodiax Poly-HRP polymer conjugated to mouse anti-human cytokeratin 8/18 antibodies, photographed digitally with 100× microscope magnifications. The examined tissue is normal prostate. Exemplary stained areas are indicated by an arrow.
Figure 6:
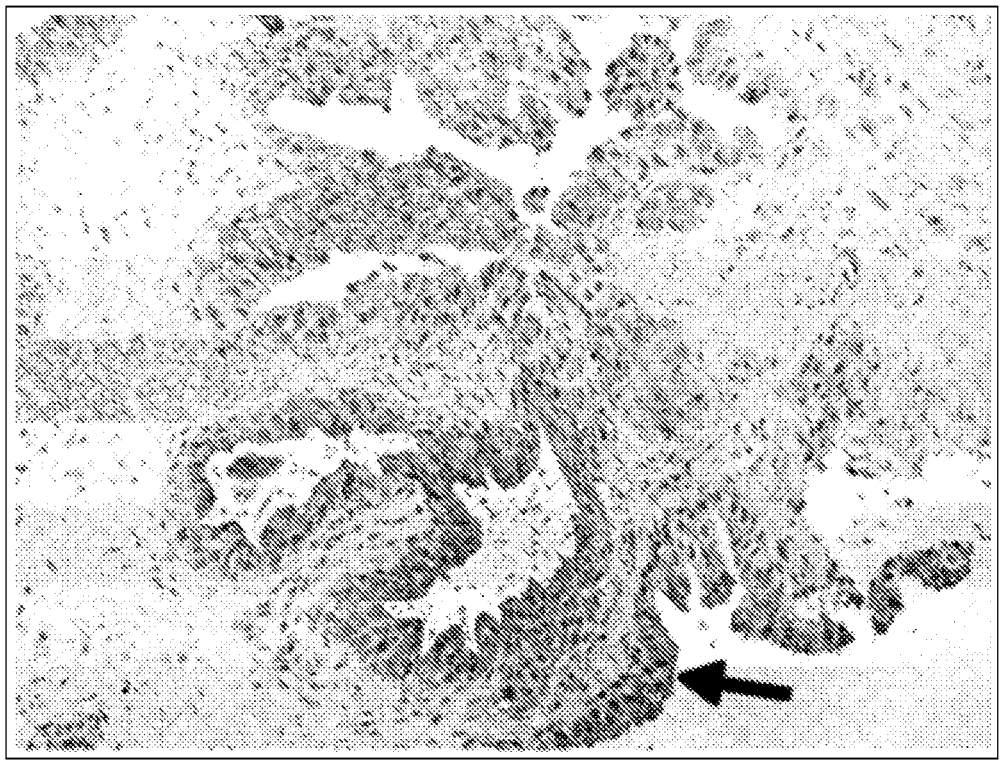
FIG. 6 depicts a representative digital micrograph (100× magnifications) of direct IHC staining using Novodiax Poly-HRP polymer conjugated to mouse anti-human prostate specific antibodies (PSA) on the normal prostate tissue. Exemplary stained areas are indicated by an arrow.
Figure 7:
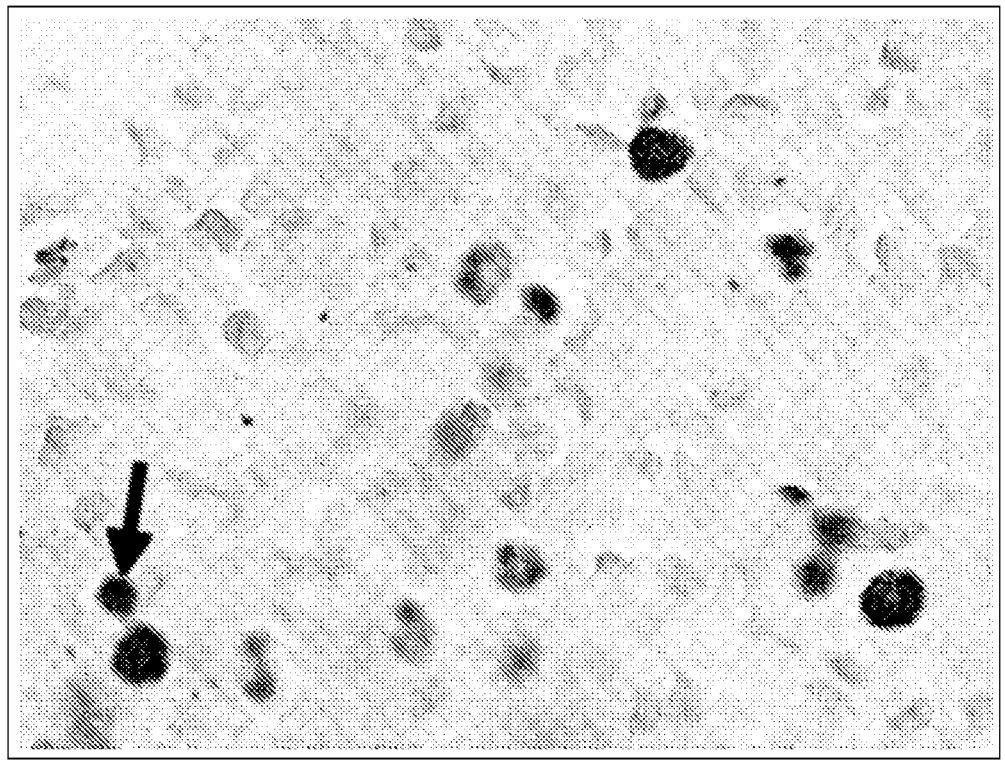
FIG. 7 depicts representative results of direct IHC staining using Novodiax Poly-HRP polymer conjugated to mouse anti-human IgG antibodies on the human lymphoid tissue. The microscope magnifitation is 400×. Exemplary stained areas are indicated by an arrow.
Figure 8:
FIG. 8 shows representative images of direct IHC staining of frozen human lymph node tissue using a poly-HRP anti-Ck8/18 antibody conjugate.
Figure 8:
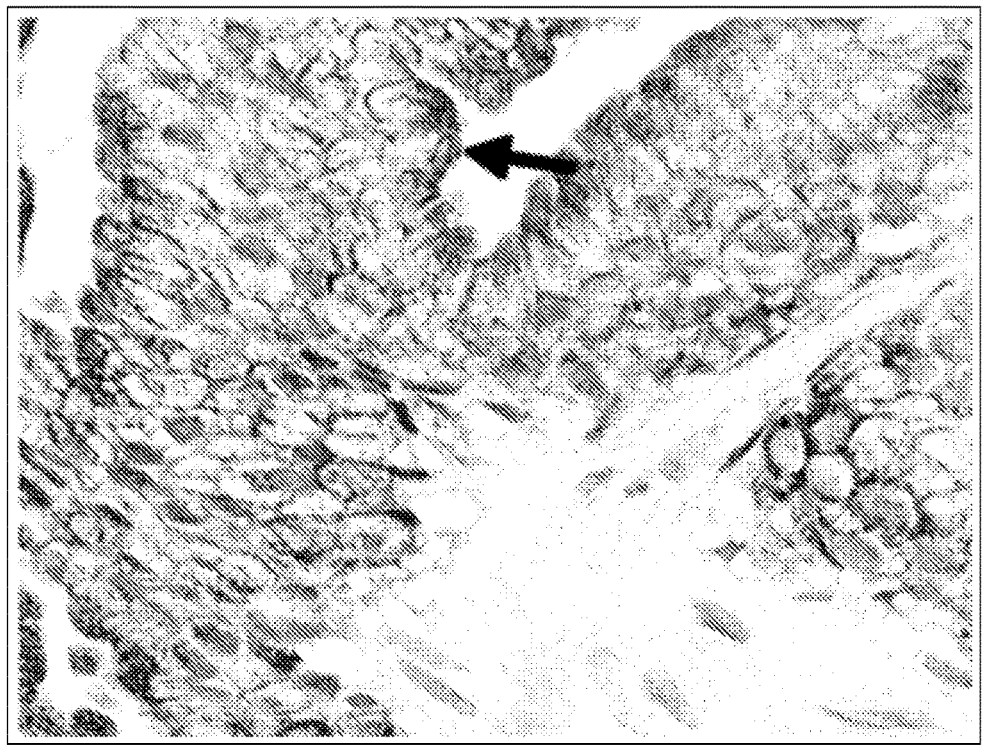

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1%, of a given value. Alternatively, particularly with respect to biological systems or processes, the term "about" can mean within an order of magnitude, preferably within 5-fold, and more preferably within 2-fold, of a value. Where particular values are described in the application and claims, unless otherwise stated, the term "about" meaning within an acceptable error range for the particular value should be assumed.

I. Immunohistochemistry Assay

In general, the present invention provides compositions, methods, and kits for detecting the presence or absence of a target analyte in a tissue sample. Generally, the method comprises: (a) contacting the tissue sample containing the target analyte with polymeric-enzyme/antibody conjugates to form a complex comprising the target analyte and at least one of the polymeric-enzyme/antibody conjugates, at an incubation temperature between about 15° C. and about 45° C. for an incubation period between about 3 minutes to about 1 hour, wherein the antibody is capable of binding specifically to the target analyte; (b) removing polymeric-enzyme/antibody conjugates that do not form the complex; (c) contacting the tissue sample with a substrate of the enzyme, thereby detecting the target analyte.

In one aspect, the compositions, methods, and kits provided are used to rapidly detect target analytes, such as antigens, in the tissue sample, such as a FFPE tissue section or a frozen tissue section. In one aspect, the compositions, methods, and kits provided are used to sensitively detect target analytes, such as antigens, in the tissue sample, such as a FFPE tissue section or a frozen tissue section. In some embodiments, the individual having a disease is selected for a treatment, wherein the detection of the target analyte by the methods disclosed herein is used as a basis to select the individual for treatment.

A. Tissue Samples

In general, the compositions and methods provided herein are used to detect the target analyte in the tissue sample derived from a subject. In some embodiments, the compositions and methods provided herein are used to detect the target analyte in the tissue derived from the subject, wherein the target analyte is a tumor antigen.

By "subject" or "patient" herein is meant any single subject for which therapy is desired, including humans, cattle, dogs, mice, rats, guinea pigs, rabbits, chickens, insects and so on. Also intended to be included as the subject is any subject involved in a clinical research trial not showing any clinical sign of disease, or the subject involved in an epidemiological study, or the subject used as a control.

By "tissue sample" herein is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue, as from a fresh, frozen, and/or preserved organ or tissue sample, or biopsy, or aspirate, or blood or any blood constituents, or bodily fluids, such as cerebral spinal fluid, amniotic fluid, peritoneal fluid, or interstitial fluid, or cells from any time in gestation or development of the subject. The tissue sample may also be primary or cultured cells or cell lines, or culture tissues. The tissue sample may contain compounds which are not naturally intermixed with the tissue in nature, such as preservatives, anticoagulants, buffers, fixatives, nutrients, antibiotics, or the like. In some embodiments of the invention, the tissue sample is "non-hematologic tissue" (i.e., not blood or bone marrow tissue).

The methods of the invention may be applied to any type of tissue, including, for example, cancer tissue. While frozen tumor tissue is not widely available, paraffin blocks are routinely prepared from tumors after surgery, allowing, for example, large-scale retrospective investigations of thymidylate synthase expression and chemotherapy response to be performed. Moreover, the technique can be applied to any of a wide range of tumor types and to an unlimited range of gene products. The methods of the invention can be used for the preparation of individual tumor "gene expression profiles," whereby expression levels could be determined in individual patient samples for one or more gene products, such as for a range of gene products that are known to influence clinical outcome and response to various chemotherapeutic agents.

In some embodiments, the tissue comprises a cancer cell. In some embodiments, the tissue comprises a cell in spatial proximity to a cancer cell. In some embodiments, the tissue comprises a cancer cell and a cell in spatial proximity to a cancer cell. In some embodiments, the tissue comprises a cell in close spatial proximity to a cancer cell. In some embodiments, the tissue comprises a normal cell in close spatial proximity to a cancer cell. In some embodiments, the tissue comprises a mixture of cancer cells and normal cells in spatial proximity to the cancer cells. In some embodiments, the mixture comprises a low percentage of cancer cells. In some embodiments, the mixture comprises less than 30%, 20%, 15%, 10%, or 5% cancer cells. In some embodiments, the mixture comprises between about 5% and about 30% cancer cells.

In some embodiments, the tissue sample comprises a tissue section.

By "section" of a tissue sample herein is meant a single part or piece of a tissue sample, for example, a thin slice of tissue or cells cut from a tissue sample. It is understood that multiple sections of tissue samples may be taken and subjected to analysis according to the present invention. In some embodiments, the selected portion or section of tissue comprises a homogeneous population of cells. In some embodiments, the selected portion or section of tissue comprises a heterogeneous population of cells. In some embodiments, the selected portion comprises a region of tissue, e.g., the lumen as a non-limiting example. The selected portion can be as small as one cell or two cells, or could represent many thousands of cells, for example. In most cases, the collection of cells is important, and while the invention has been described for use in the detection of cellular components, the method may also be used for detecting non-cellular components of an organism (e.g., soluble components in the blood as a non-limiting example).

Any tissue sample from the subject may be used. Examples of tissue samples that may be used include, but are not limited to, breast, prostate, ovary, colon, lung, endometrium, stomach, salivary gland, or pancreas. The tissue sample can be obtained by a variety of procedures including, but not limited to, surgical excision, aspiration, or biopsy. The tissue may be fresh or frozen.

In some embodiments, the tissue is aged. By "aged" herein is meant tissue that has been stored for a period of time, for example, the period of time that frozen or FFPE are stored. In some embodiments, the tissue sample is a frozen tissue sample. In some embodiments, the tissue is frozen tissue. In some embodiments, the tissue is paraffin-embedded tissue. In some embodiments, the tissue is formalin-fixed paraffin-embedded tissue.

In some embodiments, the tissue sample is a tissue section, a clinical smear, or a cultured cell or tissue. In some embodiments, the tissue is a tissue section that is more than about 5 µm thick. In some embodiments, the tissue is a tissue section that is about 5 µm thick. In some embodiments, the tissue is a tissue section that is less than about 5 µm thick. In some embodiments, the tissue is a tissue section that is about 1.5 µm thick to about 5.5 µm thick. In some embodiments, the tissue is a tissue section that is about 4.5 µm thick to about 7.5 µm thick.

In some embodiments, the tissue section is selected from the group consisting of tissue sections of brain, adrenal glands, colon, small intestines, stomach, heart, liver, skin, kidney, lung, pancreas, testis, ovary, prostate, uterus, thyroid, and spleen of a mammal. In some embodiments, the tissue section is from a solid tumor.

Preparation of Tissue Samples

The method of preparing tissue blocks from these particulate specimens has been successfully used in previous IHC studies of various prognostic factors and/or is well known to those of skill in the art.

Briefly, any intact organ or tissue may be cut into fairly small pieces and incubated in various fixatives (e.g., formalin, alcohol, etc.) for varying periods of time until the tissue is "fixed". The samples may be virtually any intact tissue surgically removed from the body. The samples may be cut into reasonably small piece(s) that fit on the equipment routinely used in histopathology laboratories. The size of the cut pieces typically ranges from a few millimeters to a few centimeters.

In some embodiments, the frozen-sections may be prepared by rehydrating 50 mg of frozen "pulverized" tissue at room temperature in phosphate-buffered saline (PBS) in a small plastic capsule; pelleting the particles by centrifugation; resuspending the particles in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent sections may be prepared by a similar method involving rehydration of the 50 mg sample in a plastic microfuge tube; pelleting; resuspending in 10% formalin for a 4 hour fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

In some embodiments, the present invention may utilize standard frozen samples, such as those that are embedded in OCT and that are not pulverized, for example, including those used in standard Frozen Section hospital labs.

Tissue samples are often fixed with a fixative. Aldehyde fixatives such as formalin (formaldehyde) and glutaraldehyde are typically used. Tissue samples fixed using other fixation techniques, such as alcohol immersion, are also suitable. See Battifora and Kopinski, J., Histochem. Cytochem., 34:1095 (1986). The samples used may also be embedded in paraffin.

In some embodiments, the tissue sample is fixed in a solution containing an aldehyde.

In some embodiments, the tissue sample is fixed in a solution containing formalin.

In some embodiments, the tissue sample is paraffin-embedded.

In some embodiments, the tissue sample is fixed and embedded in paraffin or the like.

In some embodiments, the samples are both formalin-fixed and paraffin-embedded.

In some embodiments, the formalin-fixed paraffin-embedded tissue (FFPET) block is hematoxylin and eosin stained prior to selecting one or more portions for analysis in order to select specific area(s) for the FFPET core sample.

The tissue sample may be fixed (i.e., preserved) by conventional methodology. See e.g., "Manual of Histological Staining Method of the Armed Forces Institute of Pathology," $3^{rd}$ edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of the fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's, or paraformaldehyde, may be used to fix the tissue sample.

Generally, the tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology. See, e.g., "Manual of Histological Staining Method of the Armed Forces Institute of Pathology", supra. Examples of paraffin that may be used include, but are not limited to, Paraplast, Broloid, and Tissuemay. Once the tissue sample is embedded, the sample may be sectioned by a microtome or the like. See, e.g., "Manual of Histological Staining Method of the Armed Forces Institute of Pathology", supra. By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

Deparaffinization of Samples

If paraffin has been used as the embedding material, the tissue sections are generally deparaffinized and rehydrated with water. In some embodiments, the tissue is deparaffinized prior to IHC.

Deparaffinization removes the bulk of paraffin from the paraffin-embedded sample. A number of techniques for deparaffinization are known, and any suitable technique can be used with the present invention. The preferred method of the invention utilizes washing with an organic solvent to dissolve the paraffin. Such solvents are able to remove paraffin effectively from the tissue sample without adversely affecting the ligands in the tissue. Suitable solvents can be chosen from exemplary solvents, such as benzene, toluene, ethylbenzene, xylenes, and mixtures thereof. A xylene is the preferred solvent for use in the methods of the invention. Solvents alone or in combination in the methods of the invention are preferably of high purity, usually greater than about 99%.

Paraffin is typically removed by washing with an organic solvent, with vigorous mixing followed by centrifugation. Samples are centrifuged at a speed sufficient to cause the tissue to pellet in the tube, usually at about 10,000 to about 20,000×g. After centrifugation, the organic solvent supernatant is discarded. One of skill in the art of histology will recognize that the volume of organic solvent used and the number of washes necessary will depend on the size of the sample and the amount of paraffin to be removed. The greater the amount of paraffin to be removed, the more washes will be necessary. Typically, the sample will be washed between 1 and about 10 times, and preferably, between about two and about four times. A typical volume of organic solvent is about 500 µL for a 10 µm tissue specimen.

Other methods for deparaffinization known to one of skill in the art may also be used in the method of the invention, including direct melting, for example.

In additional embodiments, citrus-based aliphatic hydrocarbons (D-Limolene based, for example) may be employed, including other exemplary proprietary formulations used for deparaffinization (e.g., HEMO-DE® (PMP Medical Industries, Inc., Irving, Tex.); CLEAR-RITE® (Microm International; Walldorf, Germany); EZ-DEWAX™ (BioGenex, San Ramon, Calif.)), for example. EZ-DEWAX™ is known to be a de-waxing and rehydration agent.

The tissue sections may be deparaffinized by several conventional standard methodologies. For example, xylenes and a gradually descending series of alcohols may be used. See, e.g., "Manual of Histological Staining Method of the Armed Forces Institute of Pathology", supra. Alternatively, commercially available deparaffinizing non-organic agents such as Hemo-De® (CMS, Houston, Tex.) may be used.

Rehydration

Samples may be rehydrated after deparaffinization. The preferred method for rehydration is step-wise washing with aqueous lower alcoholic solutions of decreasing concentration. Ethanol is a preferred lower alcohol for rehydration. Other alcohols may also be suitable for use with the invention including methanol, isopropanol and other similar alcohols in the C1-C5 range. The sample is alternatively vigorously mixed with alcoholic solutions and centrifuged. In a preferred embodiment, the concentration range of alcohol is decreased stepwise from about 100% to about 70% in water over about three to five incremental steps, where the change in solution concentration at each step is usually less than about 10% (e.g., the exemplary sequence: 100%, 95%, 90%, 80%, 70%). In some embodiments, deparaffinization and rehydration are carried out simultaneously using a reagent such as EZ-DEWAX™ (BioGenex, San Ramon, Calif.), for example.

Pretreatments

In some embodiments of the invention, the samples may be pretreated, such as to facilitate directly or indirectly the methods of the invention. In some embodiments, pretreatment of the tissue increases availability of the target analyte for antibody binding. Pretreatments for making targets available (Heat Induced Epitope Retrieval or Proteolytic Enzyme mediated) may be employed. Citrate buffers, Tris, and EDTA base may be employed as exemplary heat-induced reagents. Pepsin, Proteinase K, Trypsin, Protease, and all of the subtypes may also be employed, in certain aspects of the invention, such as by utilizing the many proprietary formulations available.

B. Target Analytes

The compositions and methods provided are used to detect one or more target analytes in the tissue sample.

By "target analyte" or "analyte" or "target" or grammatical equivalents herein is meant any molecule, compound, or particle to be detected.

In some embodiments, the target analyte is a biomarker in the diagnosis of undifferentiated neoplasma/unknown primaries, such as, epithelial markers (cytokeratins and EMA), myoepithelial markers (p63, S100, calponin, SMA, SMMH-1, CK14, maspin), mesenchymal markers (vimentin, SMA, MSA, desmin, MyoD1, Myogenin, NF, S100, P63, CD10, calponin, myoglobin, MDM2, CDK4, FLI-1, CD117, DOG1, CD31, CD34, Factor XIIIa, CD99), melanocytic markers (S100, HMB-45, MART-1, TYROSINASE, MiTF), mesothelial markers (Calretinin, CK5/6, WT1, D2-40, HBME-1, mesothelin, thrombomodulin), neuroendocrine markers (Chromogranin, synaptophysin, CD56, PGP9.5, NSE, insulin, PTH, calcitonin, thyroglobulin, prolactin), germ cell tumor markers (PLAP, OCT4, CD117 or c-kit, SALL4, CD30, alpha-fetoprotein, beta-hCG, glypican-3, inhibin-alpha, calretinin, EMA, CAM5.2), B-Cell markers (CD79a and PAX5), and hematopoietic markers (CD1a, CD2, CD3, CD5, CD10, CD38, CD21, CD35, CD15, CD30, CD79a, CD43, CD138, CD68, Bcl-2, Bcl-6, cyclin D1, MUM1, S100, MPO).

In some embodiments, the target analyte is a biomarker for identifying tumor origin, such as, calcitonin and CEA for medullary carcinoma of the thyroid; insulin, glucagon and somatostatin for pancreatic endocrine neoplasms; CK20 for merkel cell carcinoma; HMB-45, MART-1 and SMA for angiomyolipoma; S100, HMB-45, MART-1, SOX10, and vimentin for melanoma; CD117 and DOG-1 for GI and extra-GI stromal tumors; CD5 and p63 for thymic carcinoma; CK20, CDX-2, beta-catenin and villin for colorectal carcinoma; androgen receptor and GCDFP-15 for salivary duct carcinoma; GCDFP-15, ER, PR, mammaglobin for breast carcinoma; TTF1, napsin A and surfactant A for lung adenocarcinoma; TTF1, thyroglobulin, PAX8 for thyroid paoillary and follicular carcinoma; CD1a and S100 for langerhans cell histicytosis; PSA, PSAP and P504S for prostatic adenocarcinoma; CK, EMA, S100 for chordoma; P504S/KIM-1/RCCMa for papillary RCC; RCCMa, KIM-1, PAX8, pVHL for clear cell RCC; MIB1 (Ki-67) for hyalinizing trabecular adenoma of the thyroid; OCT4/CD117/PLAP/D2-40 for seminoma; CKs, desmin for desmoplastic small round cell tumor (DPSRCT); glypican-3, Hep Par1 for hepatocellular carcinoma; alpha-fetoprotein/glypican-3/PLAP/SALL4 for yolk sac carcinoma; OCT4/CD30/SOX2/SALL4/PLAP for embryonal carcinoma; DM2, CDK4 for adipose tissue/liposarcoma; myogenin, desmin, myoD1 for rhabdomyosarcoma; SAM, MSA, desmin for leiomyosarcoma/smooth muscle tumor; p16, HPV in situ for cervical and endocervical carcinoma; ER, WT1, PAX8 for ovarian serous carcinoma; CD10, ER for endometrial stromal sarcoma; maspin, VHL for pancreatic ductal adenocarcinoma (PDA); CD2, CD3 for T-cell; CD20, PAX5, CD69a for B-cell; CD43, CD34, CD33, MPO for myeloid cells; CD117, tryptase for mast cells; and CD21, CD35 for follicular dentritic cells.

In some embodiments, the target analyte is a biomarker for detailed classification within a disease category, such as, CD3, CD20, CD79a, PAX5, CD45rb, CD15, CD30, ALK-1, CD138, CD56, immunoglobulins, HHV8, EMA, TdT, CD34, CD117, and MPO for lymphomas/leukemias.

In some embodiments, the target analyte is a biomarker for companion diagnosis, such as, ER, PR, HER2, EGFR, and CD117 (c-kit).

In some embodiments, the target comprises a protein, a carbohydrate, a lipid, and/or a nucleic acid. In some embodiments, the target comprises the protein and/or characteristic portion thereof, such as, a tumor-marker, integrin, cell surface receptor, transmembrane protein, intercellular protein, ion channel, membrane transporter protein, enzyme, antibody, chimeric protein, glycoprotein, etc. In some embodiments, the target comprises the carbohydrate and/or characteristic portion thereof, such as, a glycoprotein, sugar (e.g., monosaccharide, disaccharide, polysaccharide), glycocalyx (i.e., the carbohydrate-rich peripheral zone on the outside surface of most eukaryotic cells), etc. In some embodiments, the target comprises the lipid and/or characteristic portion thereof, such as, an oil, fatty acid, glyceride, hormone, steroid (e.g., cholesterol, bile acid), vitamin (e.g. vitamin E), phospholipid, sphingolipid, lipoprotein, etc.

Numerous markers are known in the art. Typical markers include cell surface proteins, e.g., receptors. Exemplary receptors include, but are not limited to, the transferrin receptor; LDL receptor; growth factor receptors, such as epidermal growth factor receptor family members (e.g., EGFR, Her2, Her3, Her4) or vascular endothelial growth factor receptors, cytokine receptors, cell adhesion molecules, integrins, selectins, and CD molecules. The marker can be a molecule that is present exclusively or in higher amounts on a malignant cell, e.g., the tumor antigen. In some embodiments, the marker or target analyte is present in a higher amount than the marker or target analyte in a control.

In some embodiments, the target analyte is selected from: the biomarker for diagnosis of undifferentiated neoplasma and/or unknown primary tumors, selected from epithelial markers (cytokertins and EMA), myoepithelial markers (p63, S100, calponin, SMA, SMMH-1, CK14, maspin), mesenchymal markers (vimentin, SMA, MSA, desmin, MyoD1, Myogenin, NF, S100, P63, CD10, calponin, myoglobin, MDM2, CDK4, FLI-1, CD117, DOG1, CD31, CD34, Factor XIIIa, CD99), melanocytic markers (S100, HMB-45, MART-1, TYROSINASE, MiTF), mesothelial markers (Calretinin, CK5/6, WT1, D2-40, HEME-1, mesothelin, thrombomodulin), neuroendocrine markers (Chromogranin, synaptophysin, CD56, PGP9.5, NSE, insulin, PTH, calcitonin, thyroglobulin, prolactin), germ cell tumor markers (PLAP, OCT4, CD117 or c-kit, SALL4, CD30, alphafetoprotein, beta-hCG, glypican-3, inhibin-alpha, calretinin, EMA, CAM5.2), and hematopoietic markers (CD1a, CD2, CD3, CD5, CD10, CD38, CD21, CD35, CD15, CD30, CD79a, CD43, CD138, CD68, Bcl-2, Bcl-6, cyclin D1, MUMI, S100, MPO); the biomarker for identifying tumor origin, selected from: calcitonin and CEA for medullary carcinoma of the thyroid; insulin, glucagon and somatostatin for pancreatic endocrine neoplasms; CK20 for merkel cell carcinoma; HMB-4S, MART-1 and SMA for angiomyolipoma; S100, HMB-45, MART-1, SOX10, and vimentin for melanoma; CD117 and DOG-1 for GI and extra-GI stromal tumors; CD5 and p63 for thymic carcinoma; CK20, CDX-2, beta-catenin and villin for colorectal carcinoma; androgen receptor and GCDFP-15 for salivary duct carcinoma; GCDFP-15, ER, PR, mammaglobin for breast carcinoma; TTF1, napsin A and surfactant A for lung adenocarcinoma; TTF1, thyroglobulin, PAX8 for thyroid paoillary and follicular carcinoma; CD1a and S100 for langerhans cell histicytosis; PSA, PSAP and P504S for prostatic adenocarcinoma; CK, EMA, S100 for chordoma; P504S/KIM-1/RCCMa for papillary RCC; RCCMa, KIM-1, PAX8, pVHL for clear cell RCC; MIBI (Ki-67) for hyalinizing trabecular adenoma of the thyroid; OCT4/CD117/PLAP/D2-40 for seminoma; CKs, desmin for desmoplastic small round cell tumor (DPSRCT); glypican-3, Hep Par1 for hepatocellular carcinoma; alpha-fetoprotein/glypican-3/PLAP/SALL4 for yolk sac carcinoma; OCT4/CD30/SOX2/SALL4/PLAP for embryonal carcinoma; DM2, CDK4 for adipose tissue/liposarcoma; myogenin, desmin, myoD1 for rhabdomyosarcoma; SAM, MSA, desmin for leiomyosarcoma/smooth muscle tumor; p16, HPV in situ for cervical and endocervical carcinoma; ER, WT1, PAX8 for ovarian serous carcinoma; CD10, ER for endometrial stromal sarcoma; maspin, VHL for pancreatic ductal adenocarcinoma (PDA); CD2, CD3 for T-cell; CD20, PAX5, CD69a for B-cell; CD43, CD34, CD33, MPO for myeloid cells; CD117, tryptase for mast cells; or CD21, CD35 for follicular dentritic cells; the biomarker for detailed classification within a disease category, selected from CD3, CD20, CD79a, PAX5, CD45rb, CD15, CD30, ALK-1, CD138, CD56, immunoglobulins, HHV8, EMA, TdT, CD34, CD117, and MPO; or the biomarker for companion diagnosis, selected from ER, PR, HER2, EGFR, and CD117 (c-kit).

Tumor Antigens

In certain specific embodiments, the target is a tumor marker. In some embodiments, the tumor marker is an antigen that is present in a tumor that is not present in normal organs, tissues, and/or cells. In some embodiments, the tumor marker is an antigen that is associated with the tumor and is not associated with normal organs, tissues, and/or cells. In some embodiments, the tumor marker is an antigen that is on the cell surface of the tumor and is not on the cell surface of normal organs, tissues, and/or cells. In some embodiments, the tumor marker is an antigen that is more prevalent in the tumor than in normal organs, tissues, and/or cells. In some embodiments, the tumor marker is an antigen that is more prevalently associated with the tumor than normal organs, tissues, and/or cells. In some embodiments, the tumor marker is an antigen that is more prevalent in malignant cancer cells than in normal cells. In some embodiments, the tumor marker is an antigen that is more prevalently associated with malignant cancer cells than normal cells. In some embodiments, the tumor marker is present at a higher level than the tumor marker is found on the control. In some embodiments, the tumor marker is present at a higher level than the tumor marker is found on non-cancerous tissue.

In some embodiments, the target analyte comprises the tumor antigen.

By "tumor antigen" herein is meant an antigenic substance produced in tumor cells, i.e., it triggers an immune response in the host. Normal proteins in the body are not antigenic because of self-tolerance, a process in which self-reacting cytotoxic T lymphocytes (CTLs) and autoantibody-producing B lymphocytes are culled "centrally" in primary lymphatic tissue (BM) and "peripherally" in secondary lymphatic tissue (mostly thymus for T-cells and spleen/lymph nodes for B cells). Thus any protein that is not exposed to the immune system triggers an immune response. This may include normal proteins that are well sequestered from the immune system, proteins that are normally produced in extremely small quantities, proteins that are normally produced only in certain stages of development, or proteins whose structure is modified due to mutation.

In some embodiments, the target is preferentially expressed in tumor tissues and/or cells versus normal tissues and/or cells. In some embodiments, the target is expressed at a higher level in tumor tissue than normal tissue. In some embodiments, the target is expressed at a higher level than the control.

In some embodiments of the invention, the marker is the tumor marker. The marker may be a polypeptide that is expressed at higher levels on dividing than on non-dividing cells. For example, Her-2/neu (also known as ErbB-2) is a member of the EGF receptor family and is expressed on the cell surface of tumors associated with breast cancer. Another example is a peptide known as F3 that is a suitable targeting agent for directing a nanoparticle to nucleolin. See Porkka et al., Proc Natl Acad Sci, 99:7444 (2002); and Christian et al., J Cell Biol, 163:871 (2003). It has been shown that targeted particles comprising a nanoparticle and the A10 aptamer (which specifically binds to PSMA) were able to specifically and effectively deliver docetaxel to prostate cancer tumors.

Antibodies or other drugs that specifically target these tumor targets specifically interfere with and regulate signaling pathways of the biological behavior of tumor cells regulate directly, or block signaling pathway to inhibit tumor cell growth or induce apoptosis. To date, there are dozens of target drugs have been approved for solid tumors or hematological malignancies clinical research and treatment, and there are number of targeted drugs for hematological malignancies.

In some embodiments, the tumor antigen (or tumor target) is selected from the group consisting of: CD2, CD19, CD20, CD22, CD27, CD33, CD37, CD38, CD40, CD44, CD47, CD52, CD56, CD70, CD79, and CD137.

In some embodiments, the tumor antigen (or tumor target) is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y antigen, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof. The variants of the tumor antigen encompass various mutants or polymorphisms known in the art and/or naturally occurred.

In some embodiments, the target analyte is expressed at a low level. In some embodiments, the copy number of the target analyte is about $1 \times 10^3$ to $1 \times 10^4$ per cell, such as ROR1 and ROR2. See S. Baskar et al., Unique cell surface expression of receptor tyrosine kinase ROR1 in human B-cell chronic lymphocytic leukemia, Clin Cancer Res 2008:14(2) 396, V. Walkamm et al., Live Imaging of Xwnt5A-ROR2 complexes, PLOS ONE 2014 Vol 9 (10) 1-9.

C. Polymeric-Enzyme/Antibody Conjugates

In another aspect, the present inventions provide polymeric-enzyme/antibody conjugates wherein the antibody is capable of binding specifically to the target analyte.

Antibodies

In general, the conjugates comprise an antibody or a functional fragment thereof.

By immunoglobulin" or "antibody" herein is meant a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter. Such antibodies include IgG1, lgG2a, IgG3, IgG4 (and IgG4 subforms), as well as IgA isotypes.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin The terms "full-length antibody," "intact antibody," and "whole antibody" are used herein interchangeably to refer to an antibody having a structure substantially similar to a native antibody structure or having heavy chains that contain an Fc region as defined herein.

By "native antibodies" herein is meant naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

By "antibody fragment" herein is meant a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), single-domain antibodies, and multispecific antibodies formed from antibody fragments. For a review of certain antibody fragments. See Hudson et al., Nat Med 9, 129-134 (2003). For a review of scFv fragments, see, e.g., Pliickthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med, 9, 129-134 (2003); and Hollinger et al., Proc Natl Acad Sci, 90, 6444-6448 (1993). Triabodies and tetrabodies are also described in Hudson et al., Nat Med, 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B 1). Antibody fragments can be made by various techniques, including but not limited to proteolytic digestion of an intact antibody as well as production by recombinant host cells (e.g., E. coli or phage), as described herein.

By "antigen binding domain" herein is meant the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

By "variable region" or "variable domain" herein is meant the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

By "hypervariable region" or "HVR" herein is meant each of the regions of an antibody variable domain which are hypervariable in sequence and/or form structurally defined loops, "hypervariable loops." Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The antibody of the present invention can be a chimeric antibody, a humanized antibody, a human antibody, or an antibody fusion protein.

By "chimeric antibody" herein is meant a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a subhuman primate, cat or dog.

By "humanized antibody" herein is meant a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody. In some embodiments, specific residues of the framework region of the humanized antibody, particularly those that are touching or close to the CDR sequences, may be modified, for example replaced with the corresponding residues from the original rodent, subhuman primate, or other antibody.

By "human antibody" herein is meant an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet 7: 13 (1994), Lonberg et al., Nature 368:856 (1994), and Taylor et al., Int Immun. 6:579 (1994). A fully human antibody also can be constructed by genetic or chromosomal transfection methods, as well as phage display technology, all of which are known in the art. See, for example, McCafferty et al, Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g., Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated herein by reference in their entirety.

By "antibody fusion protein" herein is meant a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent, or mutlivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

In some embodiments, the antibody is selected based on its specificity for an antigen expressed on a target cell, or at a target site, of interest in the tissue sample. A wide variety of tumor-specific or other disease-specific antigens have been identified and antibodies to those antigens have been used or proposed for use in the treatment of such tumors or other diseases. The antibodies that are known in the art can be used in the compounds of the invention, in particular for the treatment of the disease with which the target antigen is associated. Examples of target antigens (and their associated diseases) to which an antibody-linker-drug conjugate of the invention can be targeted include: CD2, CD19, CD20, CD22, CD27, CD33, CD37, CD38, CD40, CD44, CD47, CD52, CD56, CD70, CD79, CD137, 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin $\alpha v$, Integrin $\alpha v \beta$, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, and VEGFR-3.

In some embodiments, the antibody is an anti-ROR2, anti-Ck8/18, anti-Ki-67, anti-Ck5, anti-Mart-1, anti-S100, or anti-CD45 antibody.

In some embodiments, the conjugate comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

In some embodiments, the conjugates comprise a primary antibody.

By "primary antibody" herein is meant an antibody that binds specifically to the target protein antigen in the tissue sample. A primary antibody is generally the first antibody used in an immunohistochemical (IHC) procedure. In some embodiments, the primary antibody is the only antibody used in an IHC procedure.

In some embodiments, the conjugates comprise a secondary antibody.

By "secondary antibody" herein is meant an antibody that binds specifically to the primary antibody, thereby forming a bridge between the primary antibody and a subsequent reagent, if any. The secondary antibody is generally the second antibody used in an immunohistochemical procedure.

In some embodiments, the antibody recognizing the target analyte is via direct binding. In some embodiments, the antibody recognizing the target analyte is via indirect binding. In some embodiments, the antibody binding specifically to the target analyte is via direct binding. In some embodiments, the antibody binding specifically to the target analyte is via indirect binding.

In some embodiments, the binding affinity of the antibody is about $10^{-7}$ to $10^{-13}$ (Kd).

Enzymes

In general, the antibody conjugate comprises a plurality of enzyme molecules. In some embodiments, the antibody conjugate comprises a plurality of enzyme molecules, wherein the plurality of enzyme molecules comprises the same enzyme type (e.g., all enzyme molecules of an antibody conjugate are horseradish peroxidase).

The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, Methods for the Preparation of Enzyme-Antibody Conjugates for use in Enzyme Immunoassay, in Methods in Enzym (ed. J. Langone & H. Van Vunakis), Academic press, New York, 73:147-166 (1981). Examples of enzyme-substrate combinations include, for example: (i) Horseradish peroxidase (HRP) with hydrogen peroxidase as a substrate, wherein the hydrogen peroxidase oxidizes a dye precursor [e.g., orthophenylene diamine (OPD) or 3,3',5,5'-tetramethyl benzidine hydrochloride (TMB)]; (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase), or fluorogenic substrate (e.g., 4-methylumbelliferyl-β-D-galactosidase).

In some embodiments, the enzyme is selected from the group consisting of: beta-D-galactosidase, glucose oxidase, horseradish peroxidase, alkaline phosphatase, beta-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

Polymeric-Enzymes

Generally, the antibody conjugate comprises a polymeric-enzyme comprising the plurality of enzyme molecules.

In some embodiments, the plurality of enzyme molecules of the polymeric-enzyme are covalently linked. In some embodiments, the plurality of enzyme molecules of the polymeric-enzyme are covalently linked via a crosslinking reagent. In some embodiments, the enzyme comprises a protein component. In some embodiments, the plurality of enzyme molecules of the polymeric-enzyme are covalently linked via a protein component. In some embodiments, the enzyme molecule comprises a polysaccharide component. In some embodiments, the plurality of enzyme molecules of the polymeric-enzyme are covalently linked via a polysaccharide component. In some embodiments, the plurality of enzyme molecules of the polymeric-enzyme are covalently linked via a polysaccharide and a protein component. In some embodiments, the plurality of enzyme molecules of the polymeric-enzyme are non-covalently linked. In some embodiments, the plurality of enzyme molecules comprises a multimeric enzyme. In some embodiments, the plurality of enzyme molecules comprises an enzyme aggregate.

Generally, the polymerization procedure is carried out under conditions which allow for controlled and reproducible formation of the polymeric-enzyme of preselected size. The concentration of the enzyme, the pH of the buffer, the stoichiometry of free functional groups relative to crosslinking reagent, the temperature, and the time of reaction are all important factors in achieving this controllable process.

In some embodiments, the polymeric-enzyme comprises about 5 to about 500 enzyme molecules. In some embodiments, the polymeric-enzyme comprises at least about 5, 10, 15, 20, 25, 50, 75, 100, 150, 200, or 250 enzyme molecules. In some embodiments, the polymeric-enzyme comprises less than about 250, 200, 150, 100, 75, 50, 25, 20, 15, 10, or 5 enzyme molecules.

In some embodiments, the enzyme molecules of the polymeric-enzyme are covalently linked via a crosslinking reagent. In some embodiments, the enzyme molecules of the polymeric-enzyme are covalently linked via a zero-length crosslinking reagent. In some embodiments, the enzyme molecules of the polymeric-enzyme are covalently linked in a linear manner. In some embodiments, the enzyme molecules of the polymeric-enzyme are covalently linked in a branched manner. In some embodiments, the enzyme molecules of the polymeric-enzyme are covalently linked in a mixed linear and branched manner. In some embodiments, the enzyme molecules of the polymeric-enzyme are covalently linked to form a linear structure. In some embodiments, the enzyme molecules of the polymeric-enzyme are covalently linked to form a globular structure.

In some embodiments, the population of polymeric-enzymes comprising a plurality of polymeric-enzymes comprises a size distribution of polymeric-enzymes as characterized by the number of enzyme molecules per polymeric-enzyme. In some embodiments, the population of polymeric-enzymes comprising the plurality of polymeric-enzymes comprises a shape distribution of polymeric-enzymes as characterized by the structure of the polymeric-enzyme.

In some embodiments, the polymeric-enzyme has a molecular weight of about 500 kDa to about 5 mega Daltons (MDa). In some embodiments, the polymeric-enzyme has a molecular weight of at least about 500 kDa. In some embodiments, the polymeric-enzyme has a molecular weight of less than or about 5 MDa. In some embodiments, the polymer-enzyme has a molecular weight of at least about 750 kDa. In some embodiments, the polymer-enzyme has a molecular weight of at least about 1, 2, 3, or 4 MDa.

In some embodiments, the polymeric-enzymes are first formed before being conjugated to antibodies.

Enzyme/Antibody Conjugates

Generally, the enzyme is conjugated to an antibody. In some embodiments, more than one enzyme molecule is conjugated to an antibody. In some embodiments, the enzyme molecule is conjugated to more than one antibody. In some embodiments, more than one antibody is conjugated to an enzyme molecule. In some embodiments, more than one enzyme molecule is conjugated to more than one antibody. In some embodiments, more than one antibody is conjugated to more than one enzyme.

By "conjugated" or "attached" or "linked" herein is meant the covalent or non-covalent, as well as direct or indirect, association of a binding agent (such as an antibody) and polymer (such as enzyme polymers) or an enzyme molecule.

Antibody conjugates contemplated in the present invention include those for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase and/or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149; and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al, 1985). The 2- and 8-azido nucleotides have also been used to map nucleotide binding domains of purified proteins (Khatoon et al, 1989; King et al, 1989; and Dholakia et al, 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors, for example, is achieved using monoclonal antibodies, and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin using reaction conditions that do not alter the antibody combining site are contemplated. Antibody conjugates produced according to this methodology are disclosed to exhibit improved longevity, specificity and sensitivity (U.S. Pat. No. 5,196,066, herein incorporated by reference). Site-specific attachment of effector or reporter molecules, wherein the reporter or effector molecule is conjugated to a carbohydrate residue in the Fc region, have also been disclosed in the literature (O'Shannessy et al., 1987).

Polymeric-Enzyme/Antibody Conjugates

Generally, the polymeric-enzyme comprising a plurality of enzyme molecules is conjugated to the antibody. In some embodiments, polymeric-enzyme/antibody conjugates are generated according to methods such as disclosed by U.S. Pat. No. 4,657,853, which is incorporated by reference in its entirety. In some embodiments, the method comprises the sequential steps of: (a) covalently coupling at least two enzyme molecules to produce the polymeric-enzyme; and (b) covalently coupling the polymeric-enzyme to an antibody or fragment thereof.

In some embodiments, the polymeric-enzyme is conjugated to a specific site on the antibody or fragment thereof. In some embodiments, the polymeric-enzyme is conjugated to one or more specific sites on the antibody or fragment thereof. In some embodiments, the polymeric-enzyme is conjugated to a random site on the antibody or fragment thereof. In some embodiments, the polymeric-enzyme is conjugated to one or more random sites on the antibody or fragment thereof. In some embodiments, the polymeric-enzyme is conjugated to the antibody or fragment thereof via an inherent or exogenous chemical characteristic of an amino acid. In some embodiments, the polymeric-enzyme is conjugated to the antibody or fragment thereof via an inherent or exogenous chemical characteristic of an amino acid residue.

In some embodiments, the antibody conjugate comprises one or more polymeric-enzyme. In some embodiments, the antibody conjugate comprises 2, 3, 4, 5, 6, 7, 8 9, 10, 15, or 20 polymeric-enzymes. In some embodiments, the antibody conjugate comprise between 1 and 20 polymeric-enzymes.

In some embodiments, the antibody conjugate comprises between about 6 to about 16, 18, 20, 22, 24, 26, 28, 30, 40, 50, 60, 80, 90, 100, 110, 120, 130, 140, 150, 160, 170, 180, 190, or 200, or more, enzyme molecules per conjugate.

In some embodiments, the antibody conjugate comprises at least between 6-24, between 6-26, between 6-28, between 6-30, between 6-40, between 6-50, between 6-60, between 6-70, between 6-80, between 6-90, or between 6-100 enzyme molecules per conjugate.

In some embodiments, the antibody conjugate comprises at least 6, 8, 10, 12, 14, 16, 18, 20, 30, 40, 50, 60, 70, 80, 90, 100, 110, 120, 130, 140, 150, 160, 170, 180, 190, or 200, but no more than 250, 300, 350, 400, or 500 enzyme molecules per conjugate.

In some embodiments, the antibody conjugate has a molecule weight of between about 400 kDa to about 500 kDa, 600 kDa, 700 kDa, 800 kDa, 900 kDa, 1000 kDa, 2000 kDa, 3000 kDa, 4000 kDa, 5000 kDa, 6000 kDa, 7000 kDa, 8000 kDa, 9000 kDa, or 10000 kDa.

In some embodiments, the antibody conjugate has a molecule weight of between about 470 kDa to about 4.7 megaDa.

In some embodiments, the polymeric-enzyme/antibody conjugate comprises more than one antibody. In some embodiments, the polymeric-enzyme/antibody conjugate comprises a plurality of polymeric-enzymes. In some embodiments, the polymeric-enzyme/antibody conjugate comprises a plurality of polymeric-enzymes, wherein each of the polymeric-enzymes comprise about the same number of the enzyme molecules. In some embodiments, the polymeric-enzyme/antibody conjugate comprises a plurality of polymeric-enzymes, wherein the plurality of polymeric-enzymes exhibit a distribution in the number of enzyme molecules of each polymeric-enzyme. In some embodiments, the polymeric-enzyme/antibody conjugate comprises a plurality of polymeric-enzymes, wherein the plurality of polymeric-enzymes exhibit differences in the shape of the polymeric-enzymes.

In some embodiments, the polymeric-enzyme/antibody conjugate has a ratio (antibody to enzyme) of greater than 1:8. In some embodiments, the polymeric-enzyme/antibody conjugate has a ratio (antibody to enzyme) of greater than 1:6. In some embodiments, the polymeric-enzyme/antibody conjugate has a ratio (antibody to enzyme) of about 1:6, 1:8, 1:15, 1:20, 1:30, 1:40, 1:50, 1:60, 1:75, 1:100, 1:125, 1:150, 1:200.

In some embodiments, the number of polymeric-enzymes conjugated to the polymeric-enzyme/antibody conjugate is adjusted to allow for increased tissue penetration and target analyte detection. In some embodiments, the weight ratio of a polymeric-enzyme/antibody conjugate is adjusted to allow for increased tissue penetration and target analyte detection. In some embodiments, the number of enzymes per polymeric-enzyme conjugated to a polymeric-enzyme/antibody conjugate allows for increased tissue penetration and target analyte detection. In some embodiments, the size of the polymeric-enzyme conjugated to a polymeric-enzyme/antibody conjugate allows for increased tissue penetration and target analyte detection.

In some embodiments, the polymeric-enzyme/antibody conjugate is the conjugate as available from Novodiax, Inc. (Hayward, Calif.), catalogue nos. K29301-1/8, Q31001, Q31002, Q31003, Q31004, Q31005, D28001, D28002, D28003, D28004, D28005, or D28006.

Enzyme Substrate

Generally, a solution comprising an enzyme-specific substrate is incubated with a polymeric-enzyme/antibody conjugate to allow for detection. In some embodiments, the solution comprising an enzyme-specific substrate is prepared from a stock solution of said enzyme-specific substrate.

In some embodiments, the solution comprising an enzyme-specific substrate, and/or stock solution enzyme-specific substrate, is free of an impurity. In some embodiments, the solution (e.g., buffer) used to prepare the solution comprising an enzyme-specific substrate, and/or stock enzyme-specific substrate solution, is free of an impurity. In some embodiments, the impurity will inhibit the catalytic reaction of the enzyme.

In some embodiments, the enzyme-specific substrate is substantial pure. In some embodiments, the purity of the enzyme-specific substrate is 80%, 85%, 90%, 95%, 99%, 99.5%, or 99.9% pure.

In some embodiments, the solution comprising an enzyme-specific substrate is prepared immediate before incubation with the polymeric-enzyme/antibody conjugate.

In some embodiments, the enzyme molecules of a polymer-enzyme catalyze more than one substrate type.

In some embodiments, the enzyme is horseradish peroxidase and the substrate is DAB (3,3'-diaminobenzidinechromogen). In some embodiments, the enzyme is horseradish peroxidase and the substrate is AEC (3-amino-9-ethylcarbazole). In some embodiments, the enzyme is horseradish peroxidase and the substrate is AMEC Red. In some embodiments, the enzyme is horseradish peroxidase and the substrate is TMB (3, 3', 5, 5'-tetramethylbenzidine). In some embodiments, the enzyme is alkaline phosphatase and the substrate is Fast Red (Sigma-Aldrich, ST. Louis, Mo.). In some embodiments, the enzyme is alkaline phosphatase and the substrate is BCIP/NBT (5-bromo-4-chloro-3-indolyl phosphate/nitroblue tetrazolium).

E. Immunodetection Methods

Two general methods of IHC are available: indirect and direct assays.

In a typical indirect assay, unconjugated primary antibody binds to the antigen and then a labeled secondary antibody binds to the primary antibody. The secondary antibody is conjugated to an enzymatic label, a chromogenic, or fluorogenic substrate to allow for visualization of the antigen. Signal amplification occurs because several secondary antibodies may react with different epitopes on the primary antibody.

In a typical direct assay, binding of antibody to the target antigen is determined directly. This direct assay uses a labeled reagent, such as a fluorescent tag or an enzyme-labeled primary antibody, which can be visualized without further antibody interaction.

Direct Assay

In one aspect, the present invention provides compositions and methods for direct IHC assay. In this direct assay, polymeric-enzyme/antibody conjugates comprising primary antibodies are used.

In some embodiments, the direct assay is used to detect a target analyte in the tissue. In some embodiments, the polymeric-enzyme/antibody conjugate is used to directly detect a target analyte in a tissue. In some embodiments, the direct IHC method is used to detect a target analyte in a tissue, wherein the method comprises use of a polymeric-enzyme/antibody conjugate. In some embodiments, the direct IHC method is used to determine the level of a target analyte in a tissue, wherein the method comprises use of a polymeric-enzyme/antibody conjugate. In some embodiments, the direct IHC method is used to determine the presence of the target analyte in the tissue, wherein the method comprises use of a polymeric-enzyme/antibody conjugate. In some embodiments, the direct IHC method is used to determine the lack of detectable presence of the target analyte in the tissue, wherein the method comprises use of a polymeric-enzyme/antibody conjugate. In some embodiments, the direct assay is used to detect a target analyte in a tissue sample (e.g., the tissue section), preferably a FFPE section or frozen tissue section.

Aside from the sample preparation procedures discussed above, further treatment of the tissue section prior to, during, or following IHC may be desired. For example, epitope retrieval methods, such as heating the tissue sample in citrate buffer may be carried out. See, e.g., Leong et al. Appl Immunohistochem 4(3):201 (1996). Following an optional blocking step, the tissue section is exposed to a primary antibody (e.g., polymeric-enzyme/antibody conjugate) for a sufficient period of time ("incubation time") and under suitable conditions such that the primary antibody binds to the target protein antigen in the tissue sample. In some embodiments, the tissue is incubated with a primary polymeric-enzyme/antibody conjugate for a sufficient period of time and under suitable conditions such that the primary polymeric-enzyme/antibody conjugate binds to the target protein antigen in the tissue. In some embodiments, the tissue is incubated with a set of primary polymeric-enzyme/antibody conjugates (e.g., more than one), wherein the set of polymeric-enzyme/antibody conjugates includes at least one polymeric-enzyme/antibody conjugate with a different target analyte binding specificity than another polymeric-enzyme/antibody conjugate in the set, for a sufficient period of time and under suitable conditions such that the primary polymeric-enzyme/antibody conjugates bind to target protein antigens in the tissue. Appropriate conditions for achieving this can be determined by routine experimentation. The extent of binding of antibody to the sample is determined by using any one of the detectable labels discussed above. Preferably, the label is an enzymatic label (e.g., HRP) which catalyzes a chemical alteration of a chromogenic substrate, such as 3,3'-diaminobenzidinechromogen. More preferably, the label is a polymeric-enzyme (e.g., poly-HRP or polymeric-HRP) which catalyzes a chemical alteration of a chromogenic substrate, such as 3,3'-diaminobenzidinechromogen.

In some embodiments, the IHC method described herein is performed in a high-throughput manner. In some embodiments, the IHC method using the polymeric-enzyme/antibody conjugate described herein is performed in a high-throughput manner. In some embodiments, the direct IHC method described herein is performed in a high-throughput manner. In some embodiments, the direct IHC method using a polymeric-enzyme/antibody conjugate described herein is performed in a high-throughput manner.

Formation of Target Analyte/Antibody Complexes

In general, the tissue sample (e.g., the tissue section) containing the target analyte is in contact with a polymeric-enzyme/antibody conjugate to form a complex comprising a target analyte and at least one of the antibody conjugates, at an incubation temperature between about 15° C. and about 50° C. for an incubation period between about 3 minutes to about 1 hour, and the antibody conjugate is a primary antibody that is capable of binding specifically to the target analyte.

In some embodiments, the tissue comprising a series target analytes (e.g., analyte A and analyte B) is in contact with a set of polymeric-enzyme/antibody conjugates (e.g., a polymeric-enzyme/antibody complex that specifically binds analyte A, and a polymeric-enzyme/antibody complex that specifically binds analyte B) to form a series of complexes comprising the target analyte and at least one of the antibody conjugates, at an incubation temperature between about 15° C. and about 50° C. for an incubation period between about 3 minutes to about 1 hour, and the antibody conjugates are primary antibodies capable of binding specifically to their respective target analytes.

In some embodiments, the IHC staining is carried out with a buffer comprising phosphate, tris, MOPS, MES, HEPES, or orbicarbonate, and optionally the buffer comprises one or more components selected from: thiomersal, proclin 300, manganese, calcium, iron, magnesium, zinc, polyethylene glycol with molecular weight from 400 to 40,000 Da, ethylene glycol, glycerol, bovine serum albumin, horse serum albumin, goat serum albumin, rabbit serum albumin, trehalose, sucrose, gelatin, Tween 20, Tween 30, dextransulfate with molecular weight from 300-30,000 Da, or DEAE dextran with molecular weight from 500-25,000 Da. The amount of each component, if included, is of the amount generally used in the art. Optimization of buffers for increasing antibody binding to target antigen, and methods of use thereof, is well known in the art.

In some embodiments, IHC staining is carried out with a buffer, such as PBS or TBS buffer, optionally with bovine serum albumin (BSA) and/or polyethylene glycol ("PEG"), such as PEGs with 200, 300, 400, 600, 1000, 1500, 2000, 3000, 4000, 50000, 6000, 10000, or 20000 molecular weight, preferably PEG 400, 1500, or 6000. In some embodiments, the buffer is a commercialized buffer from Novodiax, Inc. (Hayward, Calif.), e.g., product catalog #C30001.

In some embodiments, the incubation temperature is between about 15° C. and about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C., between about 20° C. and about 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C., between about 25° C. and about 30° C., or between about 25° C. and about 37° C.

In some embodiments, the incubation temperature is about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the incubation temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the incubation temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the incubation period is between about 3 minutes to about 5, 10, 15, 20, 25, 30, 35, 40, 45, 50, 55, or 60 minutes, between 5 minutes to about 10, 15, 20, 25, 30, 35, 40, 45, 50, 55, or 60 minutes, between 10 minutes to about 15, 20, 25, 30, 35, 40, 45, 50, 55, or 60 minutes, between about 15 minutes to about 20, 25, 30, 35, 40, 45, 50, 55, or 60 minutes, between about 20 minutes to about 25, 30, 35, 40, 45, 50, 55, or 60 minutes, between about 25 minutes to about 30, 35, 40, 45, 50, 55, or 60 minutes, between about 30 minutes to about 35, 40, 45, 50, 55, or 60 minutes.

In some embodiments, the incubation period is about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the incubation period is less than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the incubation period is greater than about 3, 4, 5, 6, 7, 8, 9, 10, 11, 12, 13, 14, 15, 16, 17, 18, 19, 20, 25, 30, 35, 40, 45, 50, 55, or 60 minutes.

Washing Step

After incubation, the tissue sample is generally washed with a washing buffer, such as such as PBS, TBS, MOPS, MES, HEPES, or bicarbonate buffer, and optionally comprising a detergent, such as Tween (e.g., 0.01-0.2%). One exemplary buffer is 10 mM PBS with 0.05% Tween 20.

The washing step is carried out 2 to 6 times, preferably 3, 4, or 5 times, for a period of 1, 2, 3, 4, 5, 6, 7, 8, 9, or 10 minutes or more per washing step.

In some embodiments, the washing temperature is between about 15° C. and about 18, 19, 20, 21, 22, 24, 25, 26, 27, 28, 29, 30, 31, 32, 33, 34, 35, 36, 37, 38, 39, 40, 41, 42, 43, 44, 45, 46, 47, 48, 49, or 50° C., between about 20° C. and about 21, 22, 24, 25, 26, 27, 28, 29, 30, 31, 32, 33, 34, 35, 36, 37, 38, 39, 40, 41, 42, 43, 44, 45, 46, 47, 48, 49, or 50° C., between about 25° C. and about 30° C., or between about 25° C. and about 37° C.

In some embodiments, the washing temperature is about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37°

C., 38° C., 39° C., 40° C., 41° C., 42° C., 43° C., 44° C., 45° C., 46° C., 47° C., 48° C., 49° C., or 50° C.

In some embodiments, the washing temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the washing temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the washing period is between about 3 minutes to about 5, 10, 15, 20, 25, 30, 35, 40, 45, 50, 55, or 60 minutes, between 5 minutes to about 10, 15, 20, 25, 30, 35, 40, 45, 50, 55, or 60 minutes, between 10 minutes to about 15, 20, 25, 30, 35, 40, 45, 50, 55, or 60 minutes, between about 15 minutes to about 20, 25, 30, 35, 40, 45, 50, 55, or 60 minutes, between about 20 minutes to about 25, 30, 35, 40, 45, 50, 55, or 60 minutes, between about 25 minutes to about 30, 35, 40, 45, 50, 55, or 60 minutes, or between about 30 minutes to about 35, 40, 45, 50, 55, or 60 minutes.

In some embodiments, the washing period is about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the washing period is less than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the washing period is greater than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the washing step is carried out 2 to 6 times, for a period of 1, 2, 3, 4, 5, 6, 7, 8, 9, or 10 minutes or more per washing step, wherein the washing temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the washing step is carried out 2 to 6 times, for a period of about 1, 2, 3, 4, 5, 6, 7, 8, 9, or 10 minutes or more per washing step, wherein the washing temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the number of washing steps for a method comprising use of a polymeric-enzyme/antibody conjugate is reduced as compared to a method using an antibody conjugated with a single enzyme molecule. In some embodiments, the length of washing steps for a method comprising use of a polymeric-enzyme/antibody conjugate is reduced as compared to a method using an antibody conjugated with a single enzyme molecule. In some embodiments, the number of washing steps and the length of washing steps for a method comprising use of a polymeric-enzyme/antibody conjugate is reduced as compared to a method using an antibody conjugated with a single enzyme molecule. In some embodiments, the stringency of the washing solution for a method comprising use of a polymeric-enzyme/antibody conjugate is greater than the stringency of a washing solution used in a method using an antibody conjugated with a single enzyme molecule. In some embodiments, the stringency of the washing solution for a method comprising use of a polymeric-enzyme/antibody conjugate is less than the stringency of a washing solution used in a method using an antibody conjugated with a single enzyme molecule.

Blocking Step

In some embodiments, the IHC staining process further comprises a blocking step prior to incubating the antibody conjugate with the tissue, wherein said blocking step comprises contacting said tissue with a blocking agent.

In some embodiments, the blocking agent comprises skim milk, BSA, cold fish skin gelatin, casein, or an animal serum.

In some embodiments, the blocking agent comprises a buffer, such as TBS or PBS with BSA.

In some embodiments, the blocking agent comprises a buffer system selected from PBS, TBS, MOPS, MES, HEPES, and bicarbonate, optionally with 0.5-6% of bovine serum albumin, horse serum albumin, goat serum albumin, rabbit serum albumin, or gelatin, and 0.001-0.05% of Tween 20.

In some embodiments, the blocking agent comprises about 1%, 2%, 3%, 4%, 5%, 6%, 7%, 8%, 9% or 10% skim milk.

In some embodiments, the blocking agent comprises about 1%, 2%, 3%, 4%, 5%, 6%, 7%, 8%, 9%, 10%, 11%, 12%, 13%, 14%, or 15% BSA.

In some embodiments, the blocking temperature is between about 15° C. and about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C., between about 20° C. and about 21, 22, 24, 25, 26, 27, 28, 29, 30, 31, 32, 33, 34, 35, 36, 37, 38, 39, 40, 41, 42, 43, 44, 45, 46, 47, 48, 49, or 50° C., between about 25° C. and about 30° C., or between about 25° C. and about 37° C.

In some embodiments, the blocking temperature is about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the blocking temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the blocking temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the blocking period is between about 3 minutes to about 5, 10, 15, 20, 25, 30, 35, 40, 45, 50, 55, or 60 minutes, between 5 minutes to about 10, 15, 20, 25, 30, 35, 40, 45, 50, 55, or 60 minutes, between 10 minutes to about 15, 20, 25, 30, 35, 40, 45, 50, 55, or 60 minutes, between about 15 minutes to about 20, 25, 30, 35, 40, 45, 50, 55, or 60 minutes, between about 20 minutes to about 25, 30, 35, 40, 45, 50, 55, or 60 minutes, between about 25 minutes to about 30, 35, 40, 45, 50, 55, or 60 minutes, or between about 30 minutes to about 35, 40, 45, 50, 55, or 60 minutes.

In some embodiments, the blocking period is about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking period is less than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking period is greater than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking step is performed 1, 2, 3, 4, or 5 times.

In some embodiments, the blocking step is performed 1, 2, or 3 times, wherein the blocking agent comprises about 1%, 2%, 3%, 4%, 5%, 6%, or 7% skim milk, and wherein the blocking period is less than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking step is performed 1, 2, or 3 times, wherein the blocking agent comprises about 1%, 2%, 3%, 4%, 5%, 6%, or 7% skim milk, and wherein the blocking period is greater than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking step is performed 1, 2, or 3 times, wherein the blocking agent comprises about 1%, 2%, 3%, 4%, 5%, 6%, or 7% BSA, and wherein the blocking period is less than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the blocking step is performed 1, 2, or 3 times, wherein the blocking agent comprises about 1%, 2%, 3%, 4%, 5%, 6%, or 7% BSA, and wherein the blocking period is greater than about 3, 4, 5, 6, 7, 8, 9, 10, 11, 12, 13, 14, 15, 16, 17, 18, 19, 20, 25, 30, 35, 40, 45, 50, 55, or 60 minutes.

In some embodiments, the tissue may also be morphologically stained. In some embodiments, the tissue may be counterstained to allow for identification of a cell or cellular component.

In some embodiments, the tissue sample may be counterstained with hematoxylin, and dehydrated for long term storage, using methods known in the art. In some embodiments, the tissue sample may be stained with H/E.

Detection Step

After the washing step, a detection agent comprising a substrate of the enzyme, such as DAB for HRP, or Fast Red for AP, is added to the tissue sample.

In some embodiments, the detection reagent comprises a buffer, such as PBS or TBS buffer, optionally with BSA and/or polyethylene glycol.

In some embodiments, the staining is carried out with a buffer comprising phosphate, tris, MOPS, MES, HEPES, or bicarbonate, and optionally comprises hiomersal, proclin 300, manganese, calcium, iron, magnesium, zinc, polyethylene glycol with molecular weight from 400 to 40,000 Da, ethylene glycol, glycerol, bovine serum albumin, horse serum abumin, goat serum albumin, rabbit serum albumin, trehalose, sucrose, gelatin, Tween 20, Tween 30, dextransulfate with molecular weight from 300-30,000 Da, or DEAE dextran with molecular weight from 500-25,000.

In some embodiments, the detection temperature is between about 15° C. and about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C., between about 20° C. and about 21, 22, 24, 25, 26, 27, 28, 29, 30, 31, 32, 33, 34, 35, 36, 37, 38, 39, 40, 41, 42, 43, 44, 45, 46, 47, 48, 49, or 50° C., between about 25° C. and about 30° C., or between about 25° C. and about 37° C.

In some embodiments, the detection temperature is about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the detection temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the detection temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the incubation period is between about 3 minutes to about 30 minutes, between about 5 minutes to about 15 minutes, or between about 3 minutes to about 5 minutes.

In some embodiments, the incubation period is about 1, 2, 3, 5, 7, 9, 10, 12, 15, 20, 25, 30, 35, 40, 45, 50, 55, or 60 minutes.

In some embodiments, the incubation period is less than about 1, 2, 3, 5, 7, 9, 10, 12, 15, 20, 25, 30, 35, 40, 45, 50, 55, or 60 minutes.

In some embodiments, the incubation period is greater than about 1, 2, 3, 5, 7, 9, 10, 12, 15, 20, 25, 30, 35, 40, 45, 50, 55, or 60 minutes.

In some embodiments, the detection temperature is about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., and the incubation period is about 1, 2, 3, 5, 7, 9, 10, 12, 15, 20, 25, 30, 35, 40, 45, 50, 55, or 60 minutes.

In some embodiments, the detection temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., and the incubation period is less than about 1, 2, 3, 5, 7, 9, 10, 12, 15, 20, 25, 30, 35, 40, 45, 50, 55, or 60 minutes.

In some embodiments, the detection temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., and the incubation period is less than about 1, 2, 3, 5, 7, 9, 10, 12, 15, 20, 25, 30, 35, 40, 45, 50, 55, or 60 minutes.

In some embodiments, the detection temperature is less than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., and the incubation period is greater than about 1, 2, 3, 5, 7, 9, 10, 12, 15, 20, 25, 30, 35, 40, 45, 50, 55, or 60 minutes.

In some embodiments, the detection temperature is greater than about 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., and the incubation period is greater than about 1, 2, 3, 5, 7, 9, 10, 12, 15, 20, 25, 30, 35, 40, 45, 50, 55, or 60 minutes.

After the incubation, the tissue sample is rinsed one or more times with water, such as tap water.

In some embodiments, the enzymatic reaction is detected using a spectrophotometer. In some embodiments, the enzymatic reaction is detected using a chemiluminometer. In some embodiments, the enzymatic reaction is detected using a fluorescent detector. In some embodiments, the enzymatic reaction is detected using a colormetric signal detector. In some embodiments, the enzymatic reaction is detected using a light microscope or a fluorescent microscope.

In some embodiments, the target analyte is quantified. In some embodiments, the target analyte is relatively quantified. In some embodiments, the target analyte is quantified relative to a standard. In some embodiments, the target analyte is quantified relative to a standard curve.

D. Morphological Staining

After preparation of the tissue section, the section mounted on slides may be stained with a morphological stain for evaluation. Generally, the section is stained with one or more dyes each of which distinctly stains different cellular components. In some embodiments, xanthine dye or the functional equivalent thereof and/or a thiazine dye or the functional equivalent thereof are used to enhance and make distinguishable the nucleus, cytoplasm, and "granular" structures within each tissue section. Such dyes are commercially available and often sold as sets. By way of example, HEMA 3® (CMS, Houston, Tex.) stain set comprises xanthine dye and thiazine dye. In some embodiments, methyleneblue may also be used. Examples of other morphological stains that may be used on the instant method include, but are not limited to, dyes that do not significantly autofluoresce at the same wavelength as another fluorescent label. One of skill in the art will appreciate that staining may be optimized for a given tissue by increasing or decreasing the length of time the slides remain in the dye.

After staining, the tissue section may be analyzed by standard techniques of microscopy. Generally, a pathologist or the like assesses the tissue for the presence of abnormal or normal cells or a specific cell type and provides the loci of the cell types of interest. Thus, for example, in a study correlating HER2/neu amplification in breast cancer, a pathologist or the like would review the slides and identify normal breast cells and abnormal breast cells.

In some embodiments, morphological staining and polymeric-enzyme/antibody conjugate staining is performed on a tissue.

II. Methods of Diagnosis

The present application in one aspect provides compositions, methods, and kits for diagnosis (e.g., companion diagnostics). Generally, the method of diagnosis comprises detecting the presence or absence (i.e., a lack of measurable level) of a target analyte in an individual via a method comprising use of a polymeric-enzyme/antibody conjugate. In some embodiments, the polymeric enzyme/antibody conjugate comprises a therapeutic antibody. By detecting the binding of a therapeutic antibody to a target analyte in an individual, the method allows one to select individuals who are particularly suitable for treatment using the therapeutic antibody.

Thus, for example, in some embodiments, there is provided a method of treating an individual having a disease (such as cancer) characterized by an abnormal level of a target analyte, comprising: 1) detecting the level or presence of the target analyte using a polymeric-enzyme/antibody conjugate comprising a plurality of enzyme molecules conjugated to an antibody recognizing the target analyte; and 2) administering to the individual an effective amount of an agent that target the target analyte. In some embodiments, the agent is an antibody that specifically binds to the target analyte. In some embodiments, the agent is the same antibody as comprised in the polymeric-enzyme antibody conjugate. In some embodiments, the disease is cancer, and the target analyte is a tumor antigen.

In some embodiments, there is provided a method of assessing suitability of an individual having a disease (such as cancer) characterized by an abnormal level of a target analyte for treatment with an agent that targets the target analyte, comprising: detecting the level presence of the target analyte using a polymeric-enzyme/antibody conjugate comprising a plurality of enzyme molecules conjugated to an antibody recognizing the target analyte, wherein the level or presence of the target analyte is used as a basis for assessing suitability of the treatment. In some embodiments, the agent is an antibody that specifically binds to the target analyte. In some embodiments, the agent is the same antibody as comprised in the polymeric-enzyme antibody conjugate. In some embodiments, the method further comprises recommending the treatment to a clinician. In some embodiments, the disease is cancer, and the target analyte is a tumor antigen.

In some embodiments, there is provided a method of selecting (including identifying) an individual having a disease (such as cancer) characterized by an abnormal level of a target analyte for treatment with an agent that targets the target analyte, comprising: detecting the level presence of the target analyte using a polymeric-enzyme/antibody conjugate comprising a plurality of enzyme molecules conjugated to an antibody recognizing the target analyte, wherein the level or presence of the target analyte is used as a basis for selecting (including identifying) the individual for treatment. In some embodiments, the agent is an antibody that specifically binds to the target analyte. In some embodiments, the agent is the same antibody as comprised in the polymeric-enzyme antibody conjugate. In some embodiments, the method further comprises recommending the treatment to a clinician. In some embodiments, the disease is cancer, and the target analyte is a tumor antigen.

In some embodiments, detection of the target antigen is performed via IHC. In some embodiments, detection of the target antigen is performed via direct IHC. In some embodiments, the agent binds directly to the target analyte. In some embodiments, the agent binds indirectly to the target analyte. In some embodiments, the agent is a small molecule-, a nucleotide-, or an amino acid-based agent. In some embodiments, the agent is an antibody or fragment thereof. In some embodiments, the antibody binds to the same epitope of the target analyte as the antibody of the polymeric-enzyme/antibody conjugate used to detect the target analyte. In some embodiments, the antibody binds to the same epitope of the target analyte with the same binding affinity as the antibody of the polymeric-enzyme/antibody conjugate used to detect the target analyte. In some embodiments, the antibody can bind a different epitope as the antibody of the polymeric-enzyme/antibody conjugate used to detect the target analyte. In some embodiments, the presence of target analyte is detected on a target tissue. In some embodiments, the disease is a cancer. In some embodiments, the individual is human.

In some embodiments, the individual is a human.

In some embodiments, the target analyte is a biomarker for companion diagnosis, such as, ER, PR, HER2, EGFR, CD117 (c-kit).

In some embodiments, the therapeutic antibody is specific to a G-Protein Coupled Receptor or an ion channel. In some embodiments, the therapeutic antibody is specific to 1-40-β-amyloid, 4-1BB, 5AC, 5T4, ACVR2B, adenocarcinomaantigen, AGS-22M6, alpha-fetoprotein, angiopoietin 2, angiopoietin 3, AOC3 (VAP-1), B7-H3, *Bacillus* anthracisanthrax, BAFF, beta-amyloid, B-lymphoma cell, C242 antigen, C5, CA-125, carbonic anhydrase 9 (CA-IX), cardiac myosin, CCL11 (eotaxin-1), CCR4, CCR5, CD11, CD18, CD125, CD140a, CD147 (basigin), CD15, CD152, CD154 (CD40L), CD19, CD2, CD20, CD200, CD22, CD221, CD23 (IgE receptor), CD25 (α chain of IL-2 receptor), CD27, CD28, CD3, CD3 epsilon, CD30 (TNFRSF8), CD33, CD37, CD38 (cyclic ADP ribose hydrolase), CD4, CD40, CD41 (integrin alpha-IIb), CD44 v6, CD5, CD51, CD52, CD56, CD6, CD70, CD74, CD79B, CD80, CEA, CEA-related antigen, CFD, ch4D5, CLDN18.2, *Clostridium difficile*, clumping factor A, CSF2, CTLA-4, DLL4, DR5, EGFL7, EGFR, endotoxin, EpCAM, CD3, episialin, ERBB3, FAP, fibrin II, beta chain, fibronectin extra domain-B, folate receptor 1, Frizzled receptor, Ganglioside GD2, Ganglioside GD3, GMCSF receptor α-chain, GPNMB, hemagglutinin, HER1, HER2/neu, HER3, HGF, HHGFR, HNGF, Hsp90, Human scatter factor receptor kinase, ICAM-1 (CD54), IFN-α, IFN-γ, IGF-1 receptor, IGF-I, IGHE, IL 20, IL-1, IL-12, IL-23, IL-17A, IL-1β, IL-22, IL23, IL-4, IL-5, IL-6, IL-6 receptor, IL9, ILGF2, integrin α4β7, integrin α5β1, integrin α7β7, integrin αIIbβ3, integrin αvβ3, interferon receptor, interferon α/β receptor, interferon gamma-induced protein, ITGA2, ITGB2 (CD18), KIR2D, Lewis-Y antigen, LFA-1 (CD11a), lipoteichoic acid, LOXL2, L-selectin (CD62L), LTA, MCP-1, Mesothelin, MS4A1, MUC1, Mucin CanAg, Myostatin, NARP-1, NCA-90 (granulocyte antigen), NGF, N-glycolylneuraminic acid, NOGO-A, Notch receptor, NRP1, OX-40, OXLDL, PCSK9, PD-1, PD-L1, PDCD1, PDCD1, PDGF-Rα, phosphate-sodium co-transporter, Phosphatidylserine, RANKL, RHD, Rhesus factor, RON, RTN4, Sclerostin, SDC1, selectin P, SLAMF7, SOST, Sphingosine-1-phosphate, TAG-72, T-cell receptor, TEM1, Tenascin C, TFPI, TGF beta 1, TGF beta 2, TGF-β, TNF-α, TRAIL-R1, TRAIL-R2, tumor antigen CTAA16.88, Tumor specific glycosylation of MUC1, TWEAK receptor, TYRP1 (glycoprotein 75), VEGF-A, VEGFR-1, VEGFR2, Vimentin, or VWF.

Methods are also provided herein of assessing whether an individual having a disease will likely respond to treatment, comprising determining the presence of a target analyte using a polymeric-enzyme/antibody conjugate.

In addition, methods are provided herein for selecting (including identifying) an individual having a disease likely to respond to treatment comprising: (a) detecting the presence of a target analyte using a polymeric-enzyme/antibody conjugate; and (b) administering an effective amount of an agent that targets the target analyte.

Also provided herein are methods of adjusting therapy treatment of an individual having a disease receiving an effective amount of an agent that targets a target analyte, the method comprising detecting the presence of the target analyte using a polymeric-enzyme/antibody conjugate in a sample isolated from the individual, and adjusting the therapy treatment based on the assessment. In some embodiments, the amount of the agent is adjusted. In some embodiments, the disease is a cancer.

In some embodiments of any of the methods herein, the methods are predictive of and/or result in a measurable reduction in tumor size or evidence of disease or disease progression, complete response, partial response, stable disease, increase or elongation of progression free survival, or increase or elongation of overall survival. In some embodiments of any of the methods above, the individual is likely to respond to an agent that targets a target analyte, if the individual has a detectable presence of the target analyte as measured by a polymeric-enzyme/antibody conjugate, and as evident by a measurable reduction in tumor size or evidence of disease or disease progression, complete response, partial response, stable disease, increase or elongation of progression free survival, increase or elongation of overall survival.

In some embodiments of the methods, there is provided a method of prolonging progression-free survival of cancer in an individual, comprising selecting an individual for treatment on the basis of the presence of a target analyte as measured by a polymeric-enzyme/antibody conjugate. In some embodiments, the method prolongs the time to disease progression by at least any of 1, 2, 3, 4, 5, 6, 7, 8, 9, 10, 11, or 12 weeks.

In some embodiments of the methods, there is provided a method of prolonging survival of an individual having cancer, comprising selecting an individual for treatment on the basis of the presence of a target analyte as measured by a polymeric-enzyme/antibody conjugate. In some embodiments, the method prolongs the survival of the individual by at least any of 1, 2, 3, 4, 5, 6, 7, 8, 9, 10, 11, 12, 18, or 24 months.

In some embodiments of the methods, there is provided a method of reducing AEs and SAEs in an individual having cancer, comprising selecting an individual for treatment on the basis of the presence of a target analyte as measured by a polymeric-enzyme/antibody conjugate. In some embodiments of any of the methods described herein, the method is predictive of and/or results in an objective response (such as a partial response or complete response).

In some embodiments of any of the methods described herein, the method is predictive of and/or results in improved quality of life.

In some embodiments, there is provided a method for determining the percentage of individuals in a population that have a measurable presence of a target analyte using a polymeric-enzyme/antibody conjugate. In some embodiments, the expression of the target analyte is determined using IHC. In some embodiments, the expression of the target analyte is determined using direct IHC. In some embodiments, the expression of the target analyte is determined using a polymeric-enzyme/antibody conjugate. In some embodiments, the expression of the target analyte is determined using direct IHC using a polymeric-enzyme/antibody conjugate. In some embodiments, the target analyte is a tumor antigen. In some embodiments, the individual is a human.

In some embodiments, there is provided a method for determining a tissue distribution of a target analyte in an individual using a polymeric-enzyme/antibody conjugate. In some embodiments, the tissue distribution of the target analyte is determined for more than one tissue type in an individual. In some embodiments, the tissue distribution of the target analyte is determined for a tissue type from one or more individuals. In some embodiments, the tissue distribution of the target analyte is determined for more than one tissue type from one or more individuals. In some embodiments, the tissue distribution of the target analyte is determined using IHC. In some embodiments, the tissue distribution of the target analyte is determined using direct IHC. In some embodiments, the tissue is a cancer. In some embodiments, the individual is a human.

In some embodiments, the methods comprising use of a polymeric-enzyme/antibody conjugate for determining the presence of a target analyte on a tissue can also stratify the presence of the target analyte on the tissue. In some embodiments, the tissue is positive for the target analyte. In some embodiments, the tissue is weakly positive for the target analyte. In some embodiments, the tissue is negative for the target analyte.

In some embodiments, the methods comprising use of a polymeric-enzyme/antibody conjugate for determining the presence of a target antigen can also detect a level of the target antigen. In some embodiments, the level of the target analyte in an individual, as determined using a polymeric-enzyme/antibody conjugate, is compared to the level of the target analyte in a control sample, also as determined using a polymeric-enzyme/antibody conjugate. In some embodiments the level of the target analyte in an individual, as determined using a polymeric-enzyme/antibody conjugate, is compared to the level of the target analyte in multiple control samples, each as determined using a polymeric-enzyme/antibody conjugate. In some embodiments, multiple control samples are used to generate a statistic that is used to classify the level of the target analyte in an individual with cancer.

The level of target analyte as determined using a polymeric-enzyme/antibody conjugate can also be useful for determining any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. In some embodiments, the level of target analyte as determined using a polymeric-enzyme/antibody conjugate can also be useful for aiding assessment in any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits.

As used herein, "based upon" or "based on" include assessing, determining, or measuring the individual's characteristics as described herein (and preferably selecting an individual suitable for receiving treatment). When the presence of or level of target analyte as determined using a polymeric-enzyme/antibody conjugate is used as a basis for selection, assessing (or aiding in assessing), measuring, or determining for methods of treatment as described herein, the level of target analyte is measured before and/or during treatment, and the values obtained can be used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; or (g) predicting likelihood of clinical benefits.

In some embodiments, the individual is human. In some embodiments, the individual is a female. In some embodiments, the individual is a male. In some embodiments, the individual is under about 65 years old. In some embodiments, the individual is at least about 65 years old, at least about 70 years old, or at least about 75 years old. In some embodiments, the individual has one or more symptoms of chronic stress, including physical and psychological stress associated with the cancer, such as anxiety, depression, headache, pain, fatigue, insomnia, anorexia, nausea, malnutrition, or any combination thereof. In some embodiments, the individual has an advanced stage of cancer, such as any of T2, T3, T4, N1, N2, N3 or M1 stage of cancer based on the TNM staging system. In some embodiments, the individual has a high tumor burden, such as a large tumor size and/or a large number of cancer cells in the tumor bed. In some embodiments, the individual has palpable lymph nodes, or has cancer cells spread to nearby lymph nodes. In some embodiments, the individual has distant tumor metastases.

In some embodiments of any of the methods, the cancer is selected from the group consisting of lung cancer, uterine cancer, kidney cancer, ovarian cancer, breast cancer, endometrial cancer, head and neck cancer, pancreatic cancer, and melanoma. In some embodiments, the cancer is selected from the group consisting of breast cancer, lung cancer, and pancreatic cancer. In some embodiments, the cancer is triple negative breast cancer (TNBC). In some embodiments, the cancer is non-small cell lung cancer (NSCLC). In some embodiments, the cancer is pancreatic ductal adenocarcinoma (PDAC). In some embodiments, the cancer is selected from the group consisting of adrenocortical cancer, bile duct cancer, bladder cancer, breast cancer, cervical cancer, colon cancer, endometroid cancer, esophageal cancer, glioblasoma, head and neck cancer, kidney chromophobe cancer, kidney clear cell carcinoma, kidney papillary cell carcinoma, liver cancer, lower grade glioma, lung adenocarcinoma, lung squamous cell carcinoma, melanoma, mesothelioma, ocular melanomas, ovarian cancer, pancreatic cancer, pheochromocytoma and paraganglioma, prostate cancer, sarcoma, stomach cancer, testicular cancer, thyroid cancer, and uterine carcinosarcoma.

In some embodiments, the cancer is a solid epithelial tumor or a sarcoma. In some embodiments, the cancer is selected from a group consisting of adrenocortical carcinoma, Kaposi sarcoma, anal cancer, gastrointestinal carcinoid tumor, basal cell carcinoma, bile duct cancer, bladder cancer (such as bladder transitional cell carcinoma, bladder squamous cell carcinoma, and bladder adenocarcinoma), bone cancer (such as Ewing Sarcoma, osteosarcoma, chondrosarcoma, and malignant fibrous histiocytoma), breast cancer (such as ductal carcinoma, lobular carcinoma, fibroadenoma), bronchial tumor, carcinoma of unknown primary, cervical cancer, chordoma, colon cancer, rectal cancer, endometrial cancer, esophageal cancer (including esophageal squamous cell carcinoma and esophageal adenocarcinoma), intraocular melanoma, ovarian cancer (such as ovarian epithelial cancer, Fallopian tube cancer, and peritoneal cancer), gallbladder cancer, gastric cancer, head and neck cancer (such as hypopharyngeal cancer, laryngeal cancer, lip and oral cavity cancer, metastatic squamous neck cancer with occult primary treatment, nasopharyngeal cancer, oropharyngeal cancer, paranasal sinus and nasal cavity cancer, salivary gland cancer, and oral complications of chemotherapy and head/neck radiation), heart tumor (such as rhabdomyoma, myxoma, fibroma, fibrosarcoma, and angiosarcoma), hepatocellular (liver) cancer, kidney cancer (such as renal cell cancer, transitional cell cancer of the renal pelvis and ureter, and Wilms tumor), lung cancer (such as non-small cell lung cancer, and small cell lung cancer), skin cancer (such as basal cell carcinoma, squamous cell carcinoma, neuroendocrine carcinoma of the skin, melanoma, and Merkel cell carcinoma), pancreatic cancer, pheochromocytoma, parathyroid cancer, penile cancer, pituitary tumor, prostate cancer, uterine sarcoma (such as leiomyosarcoma and endometrial stromal sarcoma), small intestine cancer (such as small intestine adenocarcinoma and small intestine sarcoma, and gastrointestinal stromal tumor), soft tissue sarcoma (such as adult soft tissue sarcoma, and childhood soft tissue sarcoma), thyroid cancer (such as papillary, follicular, medullary and anaplastic thyroid cancer), urethral cancer (including urethral transitional cell carcinoma, urethral squamous cell carcinoma, and urethral adenocarcinoma), vaginal cancer (such as vaginal squamous cell carcinoma and vaginal adenocarcinoma), and vulvar cancer.

In some embodiments of the methods, the method is first-line therapy.

In some embodiments, the cancer is at an advanced stage (such as stage III or stage IV). In some embodiments, the cancer is metastatic cancer.

The classification or ranking of the target analyte level (i.e., high or low) as determined using a polymeric-enzyme/antibody conjugate may be determined relative to a statistical distribution of control levels. In some embodiments, the classification or ranking is relative to a control sample, such as a normal tissue. In some embodiment, the level of the target analyte is classified or ranked relative to a statistical distribution of control levels. In some embodiments, the level of the target analyte is classified or ranked relative to the level from a control sample obtained from the individual.

Control samples can be obtained using the same sources and methods as non-control samples. In some embodiments, the control sample is obtained from a different individual (for example an individual not having cancer, an individual having a benign or less advanced form of a disease corresponding to the cancer, and/or an individual sharing similar ethnic, age, and gender identity). In some embodiments, when the sample is a tumor tissue sample, the control sample may be a non-cancerous sample from the same individual. In some embodiments, multiple control samples (for example from different individuals) are used to determine a range of levels of target analytes in a particular tissue, organ, or cell population.

In some embodiments, bioinformatics methods are used for the determination and classification of the levels of the target analyte.

In some embodiments, the target analyte level is determined using a polymeric-enzyme/antibody conjugate, for example by direct immunohistochemistry. For example, the criteria for low or high levels can be made based on the number of positive staining cells and/or the intensity of the staining, for example by using an antibody that specifically recognizes the target analyte. In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining. In some embodiments, the level is high if more than about 40%, 45%, 50%, 55%, 60%, 65%, 70%, 75%, 80%, 85%, or 90%, cells have positive staining.

In some embodiments, the level is high if the staining of a polymeric-enzyme/antibody conjugate is as intense as positive control staining. In some embodiments, the level is high if the staining of a polymeric-enzyme/antibody conjugate is 80%, 85%, or 90% as intense as positive control staining of a polymeric-enzyme/antibody conjugate.

In some embodiments, strong staining, moderate staining, and low staining are calibrated levels of staining of a polymeric-enzyme/antibody conjugate, wherein a range is established and the intensity of staining is binned within the range. In some embodiments, strong staining is staining of a polymeric-enzyme/antibody conjugate above the 75th percentile of the intensity range, moderate staining is staining of a polymeric-enzyme/antibody conjugate from the 25th to the 75th percentile of the intensity range, and low staining is staining is staining of a polymeric-enzyme/antibody conjugate below the 25th percentile of the intensity range. In some aspects one skilled in the art, and familiar with a particular staining technique, adjusts the bin size and defines the staining categories.

In some embodiments, the assessment and scoring of the target analyte level as in a sample, patient, etc., as determined by a polymeric-enzyme/antibody conjugate is performed by one or more experienced clinicians, i.e., those who are experienced with target analyte expression and target analyte staining patterns using a polymeric-enzyme/antibody conjugate. For example, in some embodiments, the clinician(s) is blinded to clinical characteristics and outcome for the samples, patients, etc. being assessed and scored.

In some embodiments, the methods described herein are performed in a clinic. In some embodiments, the methods described herein are performed outside of a clinic. In some embodiments, the methods described herein are performed at a diagnostic lab.

III. Kits

In a further aspect, the present invention provides kits containing one or more of the compositions of the invention and directions for using the composition and/or carried out the disclosed methods.

In some embodiments, the present invention provides immunodetection kits for use with the immunodetection methods described above. As the antibodies are generally used to detect wild-type and/or mutant proteins, polypeptides and/or peptides, the antibodies will preferably be included in the kit. The immunodetection kits will thus comprise, in suitable container means, the primary antibody that binds to a wild-type and/or mutant protein, polypeptide and/or peptide, and/or optionally, an immunodetection reagent and/or further optionally, the wild-type and/or mutant protein, polypeptide and/or peptide.

The immunodetection reagents of the kit may take any one of a variety of forms, including those detectable labels that are associated with and/or linked to the given primary antibody, preferably as polymeric-enzyme/antibody conjugates.

The kits may further comprise a suitably aliquoted composition of the wild-type and/or mutant protein, polypeptide and/or polypeptide, whether labeled and/or unlabeled, as may be used to prepare the standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will generally include at least one vial, test tube, flask, bottle, syringe and/or other container means, into which the antibody may be placed, and/or preferably, suitably aliquoted. The kits of the present invention will also typically include a means for containing the antibody, antigen, and/or any other reagent containers in close confinement for commercial sale. Such containers may include injection and/or blow-molded plastic containers into which the desired vials are retained.

The kits of the invention are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

For example, in one embodiment of the invention, a kit will assess comprehensive panels of molecules (e.g. clinically relevant prognostic and predictive factors in cancer) in broad clinical and research settings.

In some embodiments, the kit will further comprise instructions for use in accordance with any of the methods described herein. The kit may comprise a description on selection of an individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) the polymeric-enzyme/antibody conjugate. In some embodiments, the kit comprises a) the polymeric-enzyme/antibody conjugate, and b) instructions for use. In some embodiments, the kit comprises a) a polymeric-enzyme/antibody conjugate, and b) a substrate of the polymeric-enzyme. In some embodiments, the kit comprises a) a polymeric-enzyme/antibody conjugate, b) a substrate of the polymeric-enzyme, and c) instructions for use. In some embodiments, the polymeric-enzyme is a polymeric-HRP. In some embodiments, the antibody is a therapeutic antibody.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The present invention is further exemplified, but not limited, by the following Examples that illustrate the preparation of the compounds of the invention.

Example 1

Protocol of Direct IHC on Frozen Tissue Slides

This example demonstrates a protocol for performing direct IHC on a tissue section obtained from a frozen tissue sample.

Tissue sections are prepared as described in the following exemplary method. A freshly dissected tissue block (<5 mm thick) is placed on to a pre-labeled tissue base mold. The entire tissue block is covered with cryo-embedding media (e.g., OCT). The base mold containing the tissue block is slowly placed into liquid nitrogen, submerging the entire tissue block in liquid nitrogen to ensure the tissue block is completely frozen. The frozen tissue block is transferred to a cryotome cryostat (e.g., −20° C.). The frozen tissue block is sectioned into a desired thickness (typically 5-10 μm) using the cryotome. A tissue section is placed on to a glass slide suitable for immunohistochemistry (e.g., Superfrost® Plus, VWR).

Tissue sections are immunostained as described in the following exemplary method. A tissue section is fixed with a fixative containing 75% of methanol, 5% of glacial acidic acid, and 20% of 37% formaldehyde for 1 to 2 minutes. Next the slide with the tissue section is blocked with a blocking buffer, for example, 5% skim milk or 2% BSA, for 2 minutes. Following blocking, the slide is rinsed in 10 mM phosphate buffered saline (PBS) at a neutral pH for 10 seconds; the slide is rinsed 3 times. A polymeric-HRP/antibody conjugate diluted with 1% BSA is applied to the slide to cover the whole area of the tissue section and incubated for 3 to 5 minutes at room temperature. Following incubation, the slide is washed with PBS buffer 3 times for 10 seconds each time. A DAB solution is applied to the slide to cover the whole are of the tissue section and incubated for 1 to 3 minutes. The reaction is stopped by washing with tap water. The slide is counter stained with hematoxlin for 10 seconds and then washed with water. Subsequently, the slide is briefly immersed in Acid Alcohol (0.25% Acid Alcohol Solution, by combining 11 mL concentrated Hydrochloric Acid and 4400 mL 80% Ethanol); the slide is immersed 1 to 3 times. Next the slide is briefly immersed in Lithium Carbonate (Lithium Carbonate Solution by combining 2.3 g Lithium Carbonate and 200 mL 80% Ethanol) for 15 seconds and then rinsed in tap water for 10 seconds. The slide is then immersed in 100% ethanol three time for 10 seconds each to dehydrate the tissue section. Following dehydration, clear the slide by immersing in Xylene three times for 10 seconds each.

Example 2

Deparaffinization and Re-Hydration of Tissue Slide

This example demonstrates a protocol for performing direct IHC on a tissue section following deparaffinization, re-hydration, and epitope retrieval of the tissue section.

The slide with a tissue section is immersed in xylene for 5 minutes. The xylene immersion is repeated with clean xylene two more time for 5 minutes each. Next, the slide is immersed in the following series of ethanol solutions: 100% ethanol for 3 minutes; 100% ethanol for 3 minutes; 95% ethanol for 3 minutes; and 75% ethanol for 3 minutes. The slide is subsequently rinsed in tap water by immersing the slide in clean tap water for three minutes; repeat two additional times.

Following re-hydration of the tissue section, protein epitopes are exposed using trypsin. First, a 0.1% trypsin solution is prepared in 0.1% calcium chloride using distilled water. The pH of the trypsin solution is adjusted to 7.2 using 1M sodium hydroxide. A humidifying chamber, the 0.1% trypsin solution, and the slide with the tissue section in distilled water are pre-warmed at 37° C. Subsequently, the slide with the tissue section is incubated in 0.1% trypsin solution for 20 minutes. Next, the slide is allowed to cool for 10 minutes at room temperature. After 10 minutes, the slide is rinsed in tap water by immersing the slide in clean tap water for 2 minutes; repeat one additional time. The slide is then blocked in a 3% hydrogen peroxide solution for 2 minutes. The slide is then rinsed in PBS with 0.05% Tween 20 by immersing the slide for 2 minutes; repeat one additional time. Subsequently, the slide is blocked in 1% BSA for 30 minutes.

Following blocking, the tissue section is immunostained with a polymeric-HRP/antibody conjugate. A solution comprising an polymeric-HRP/antibody conjugate is applied to the slide to cover the whole area of the tissue section and incubated for 5 to 30 minutes at room temperature. Following incubation, the slide is washed with PBS Tween 20 buffer 3 times for two minutes each time.

A DAB solution containing 30 µl chromogen/1 mL diluent is applied to the slide to cover the whole are of the tissue section and incubated for 5 minutes at room temperature. The reaction is stopped by washing with tap water. The slide is counter stained with hematoxlin for 10 seconds and then washed with water. The slide is then immersed in 0.1% sodium carbonate pH8 (bluing solution) for 15 seconds. Subsequently, the tissue section on the slide is dehydrated by immersing the slide in the following solution: 95% ethanol for 3 minutes; 100% ethanol for 3 minutes; and 100% ethanol for 3 minutes. This is followed by 2, 5 minutes washes in xylene. Subsequently, clear the slide by immersing the slide in xylene twice for 10 seconds each time.

Example 3

Direct IHC Using a Polymeric-HRP Anti-Ck8/18 Antibody Conjugate

This example demonstrates detection of Ck8/18 in tissue samples using direct IHC staining with a polymeric-HRP anti-Ck8/18 antibody conjugate.

A FFPE prostate tissue section and frozen human lymph node tissue section were prepared and immunostained using the techniques described in Example 1 and 2. The FFPE prostate tissue section was processed using trypsin to retrieve protein epitopes and a polymeric-HRP conjugated anti-Ck8/18 mouse monoclonal antibody was incubated with the tissue sample for 5 minutes at 37° C. The frozen human lymph node tissue section was incubated with a polymeric-HRP conjugated anti-Ck8/18 mouse monoclonal antibody for 3 minutes at room temperature.

Figure 9:
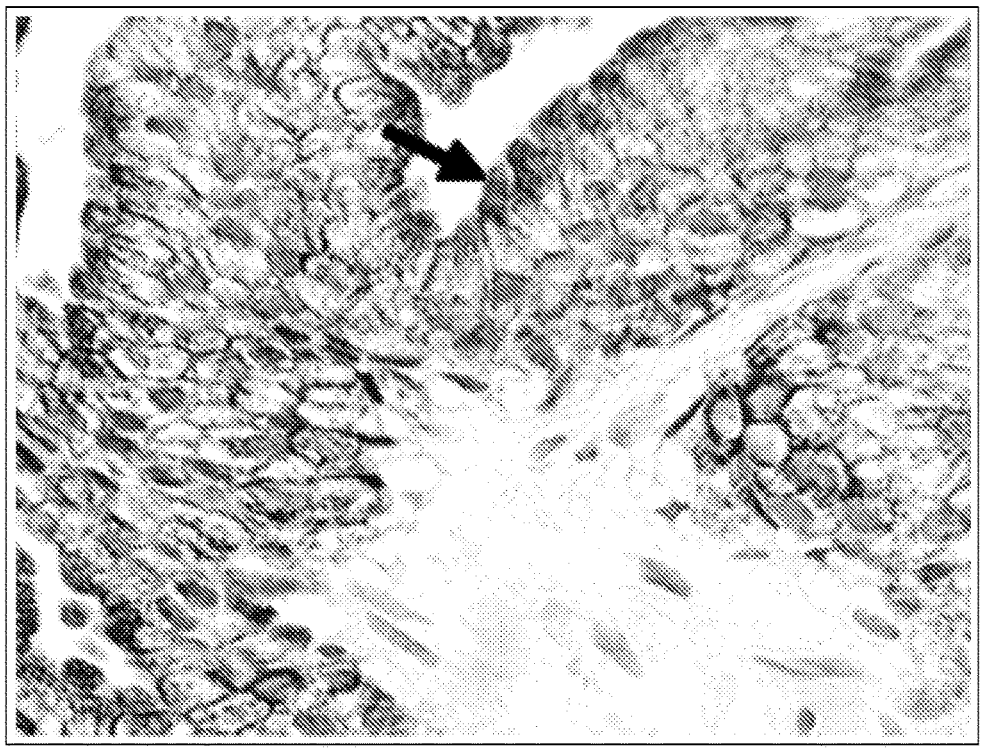
FIG. 9 shows representative images of direct IHC staining of tissue sections using a polymeric-HRP anti-Ck8/18 antibody conjugate. A FFPE prostate tissue section (FIG. 9A) and a frozen human lymph node tissue section (FIG. 9B) are illustrated. Exemplary stained areas are indicated by an arrow.
Figure 9:
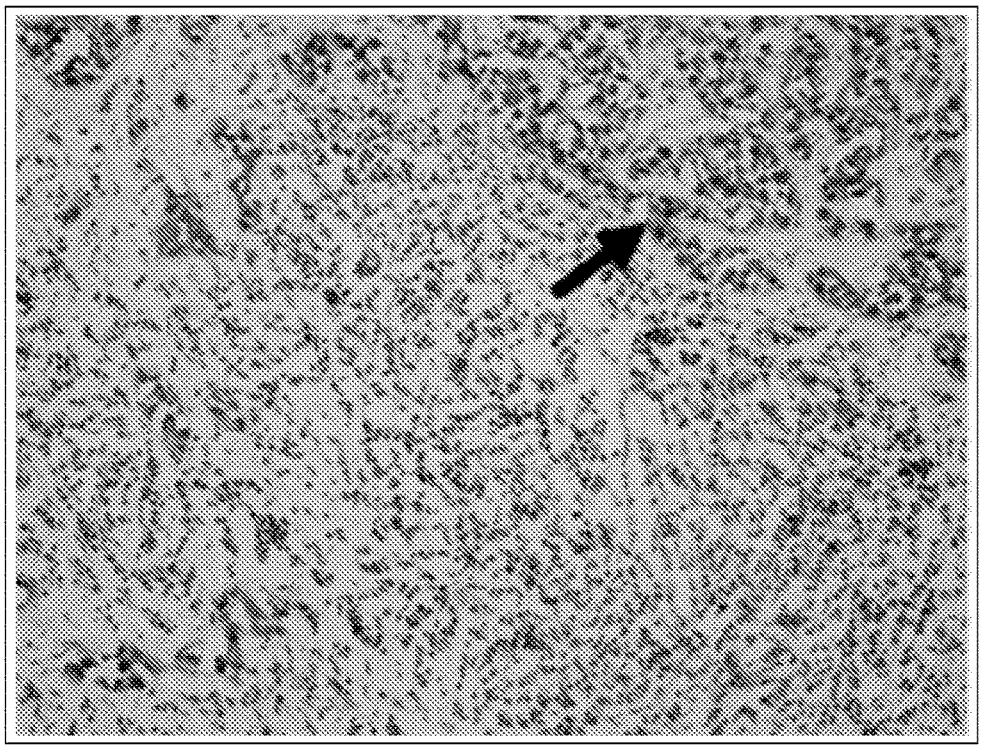

Representative images of stained cancer tissue are provided for the FFPE prostate tissue section (FIG. 9A) and the frozen human lymph node tissue section (FIG. 9B).

Example 4

Direct IHC Using a Polymeric-HRP Anti-Ki-67 Antibody Conjugate

This example demonstrates detection of Ki-67 in a tissue sample using direct IHC staining with a polymeric-HRP anti-Ki-67 antibody conjugate.

A human tonsil tissue section was prepared and immunostained using the techniques described in Example 1 and 2. Additionally, the tissue section was stained with Q-stain.

Figure 10:
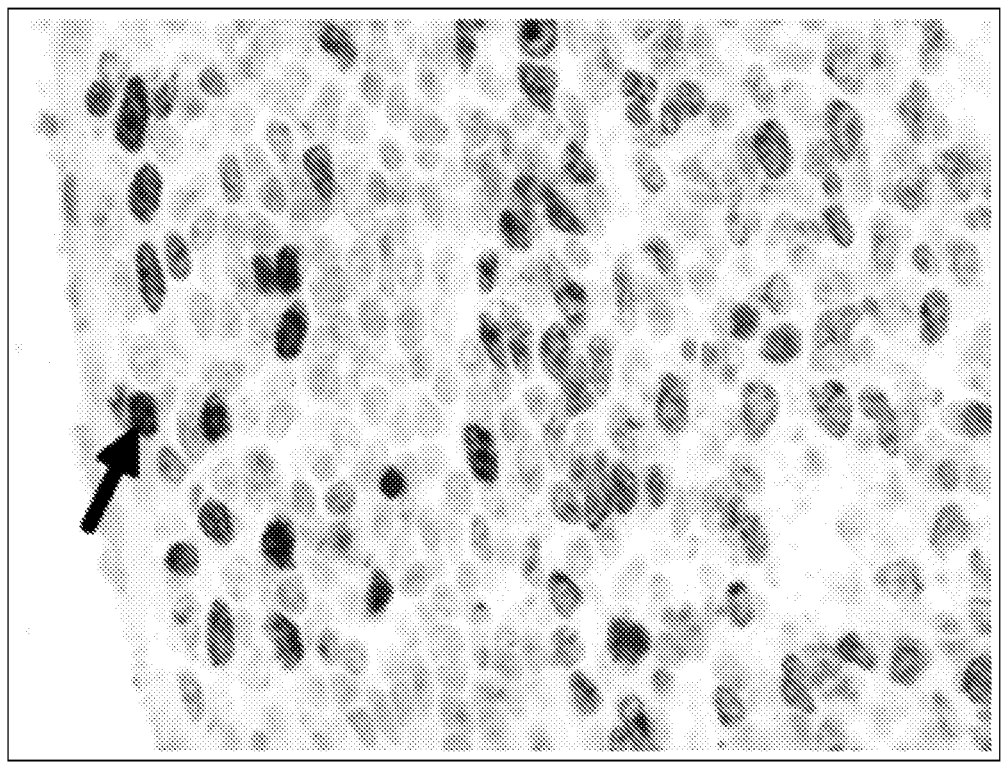
FIG. 10 shows a representative image of direct IHC staining of a human tonsil tissue section using a polymeric-HRP anti-Ki-67 antibody conjugate. Exemplary stained areas are indicated by an arrow.

A representative image of anti-Ki-67 stained tissue is provided for the human tonsil tissue section (FIG. 10).

Example 5

Direct IHC Using a Polymeric-HRP Anti-Ck5 Antibody Conjugate

This example demonstrates detection of Ck5 in a human tonsil tissue sample using direct IHC staining with a polymeric-HRP anti-Ck5 antibody conjugate.

A frozen human tonsil tissue section was prepared and immunostained using the techniques described in Example 1 and 2. The frozen human tonsil tissue section was incubated with a polymeric-HRP anti-Ck5 antibody conjugate for 10 minutes at room temperature.

Figure 11:
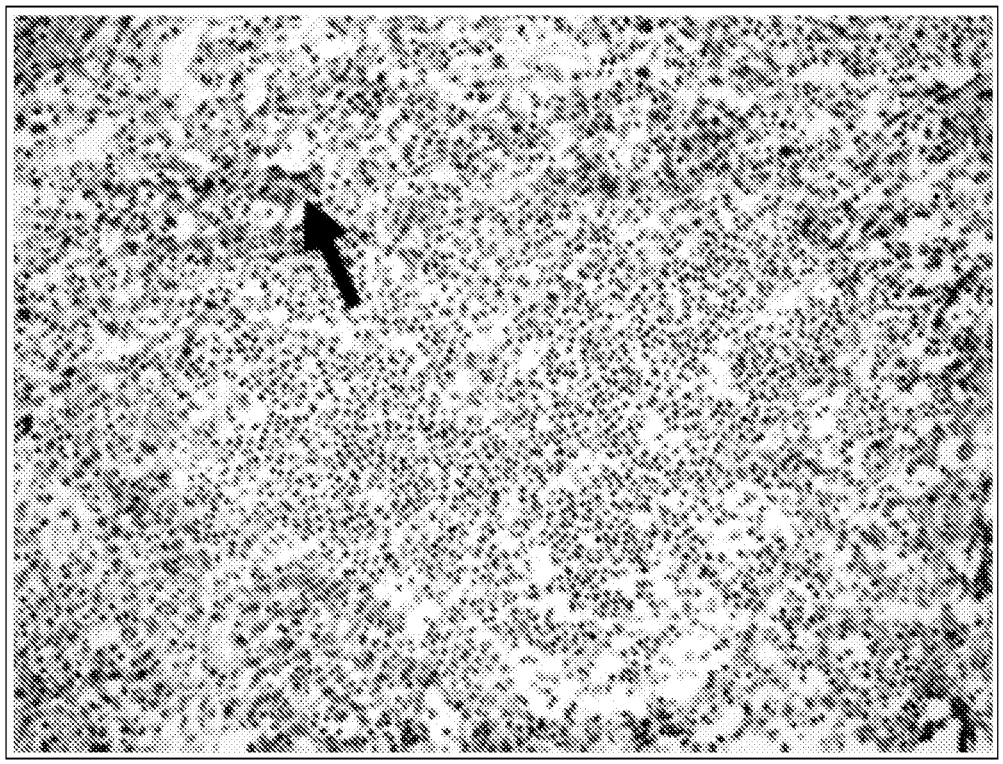
FIG. 11 shows a representative image of direct IHC staining of a human frozen tonsil tissue section using a polymeric-HRP anti-Ck5 antibody conjugate. Exemplary stained areas are indicated by an arrow.

A representative image of anti-Ck5 stained tissue is provided for the human tonsil tissue section (FIG. 11).

Example 6

Direct IHC Using a Polymeric-HRP Anti-Mart-1 Antibody Conjugate

This example demonstrates detection of Mart-1 in a melanoma tissue sample using direct IHC staining with a polymeric-HRP anti-Mart-1 antibody clone A103 conjugate.

A melanoma tissue section was prepared and immunostained using the techniques described in Example 1 and 2.

Figure 12:
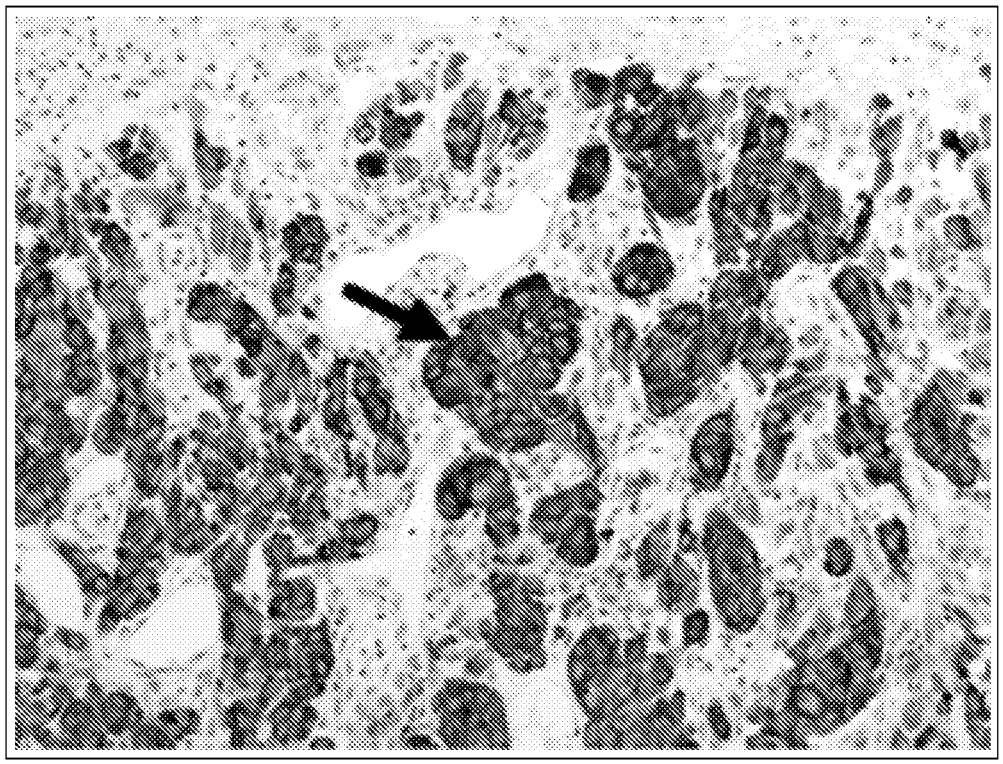
FIG. 12 shows a representative image of direct IHC staining of a melanoma tissue section using a polymeric-HRP anti-Mart-1 antibody clone A103 conjugate. Exemplary stained areas are indicated by an arrow.

A representative image of anti-Mart-1 stained tissue is provided for the melanoma tissue section (FIG. 12).

Example 7

Direct IHC Using Polymeric-HRP Anti-CD45 Antibody Conjugate

This example demonstrates detection of CD45 in a tonsil tissue sample using direct IHC staining with a polymeric-HRP anti-CD45 antibody clone 3A4 conjugate.

A tonsil tissue section was prepared and immunostained using the techniques described in Example 1 and 2.

Figure 13:
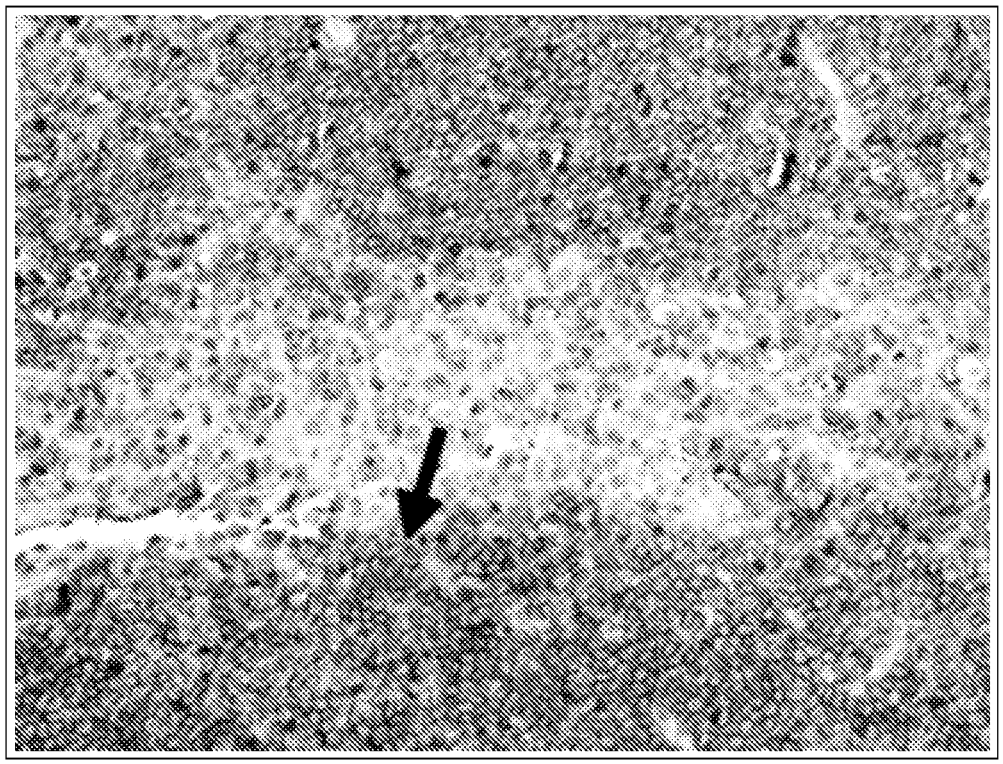
FIG. 13 shows a representative image of direct IHC staining of a tonsil tissue section using a polymeric-HRP anti-CD45 antibody clone 3A4 conjugate. Exemplary stained areas are indicated by an arrow.

A representative image of anti-CD45 stained tissue is provided for the tonsil tissue section (FIG. 13).

Example 8

Method and Results of Direct IHC Using a Therapeutic Antibody

This example demonstrates a method of direct IHC staining of a variety of tissue samples using a therapeutic antibody conjugated with polymeric-HRP.

A human therapeutic antibody that specifically binds ROR2 was obtained. The therapeutic antibody was labeled with polymeric-HRP to produce a polymeric-HRP conjugate of the therapeutic antibody.

Tissue sections were prepared and immunostained using the techniques described here, such as those described in Example 1 and 2.

Immunostained images were scored "0-4" with 4 as strongest, "3-4" as positive, "1-2" as weak positive and 0 as negative.

Working conditions of the polymeric-HRP anti-ROR2 antibody conjugate were optimized based on tissue sections known to express or lack expression of ROR2. Staining classification results of known positive and negative tissue sections are reported in Table 1. The identification of tissue expressing ROR2 with the present method correlated with the known expression of ROR2 in the tissue samples.

TABLE 1

Staining classification of tissue samples.

| Tissue sample | Staining classification |
| --- | --- |
| Stomach | Positive |
| Kidney | Positive |

TABLE 1-continued

Staining classification of tissue samples.

| Tissue sample | Staining classification |
|---|---|
| Tonsil | Negative |
| Skin | Negative |
| Breast | Negative |
| Muscle | Negative |
| Mucosa | Negative |
| Colon | Negative |
| Appendix | Negative |
| Lung | Negative |
| Liver | Negative |
| Adrenal | Negative |
| Thyroid | Negative |
| Pancreas | Negative |
| Placenta | Negative |
| Prostate | Negative |

Figure 14:
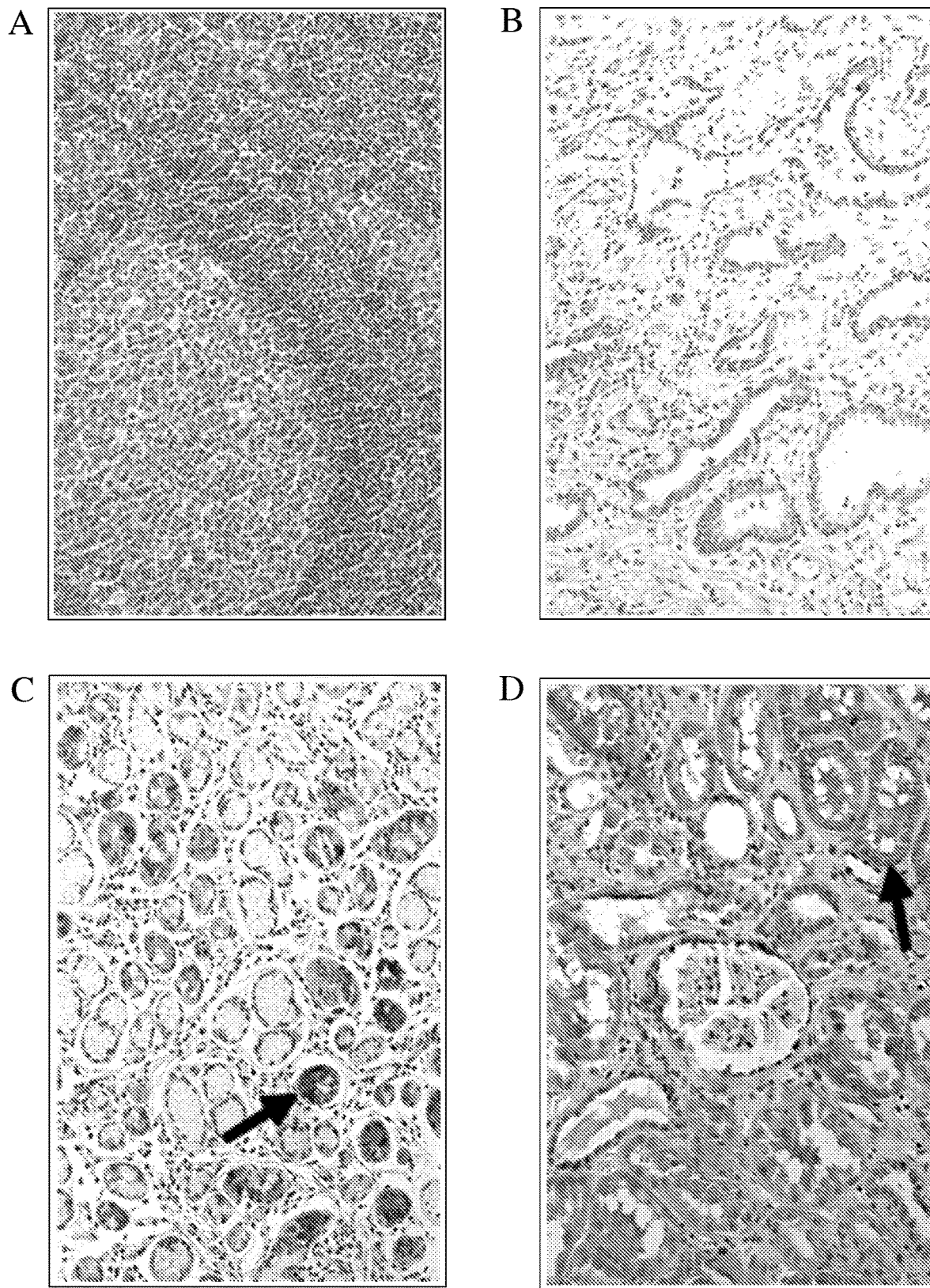
FIG. 14 shows representative images of direct IHC staining of tissue sections using a therapeutic antibody conjugated with polymeric-HRP. Tonsil (FIG. 14A), prostate (FIG. 14B), stomach (FIG. 14C), and kidney (FIG. 14D) tissue samples are illustrated. Exemplary stained areas are indicated by an arrow.

Representative images of stained tissue are provided for the following: tonsil (FIG. 14A), prostate (FIG. 14B), stomach (FIG. 14C), and kidney (FIG. 14D).

Subsequently, the optimized direct IHC method using the polymeric-HRP anti-ROR2 antibody conjugate was used to classify a series of cancer tissue samples. Staining classification results are reported in Table 2.

TABLE 2

ROR2 staining classification of cancer tissue samples.

| Cancer tissue sample | ROR2 staining classification |
|---|---|
| Melanoma | Positive |
| Neuroendocrine tumor | Positive |
| Hepatocellular carcinoma | Positive |
| Renal clear cell carcinoma | Positive |
| Lung adenocarcinoma | Weak positive |
| Large B cell lymphoma | Negative |
| Breast cancer | Negative |
| Colonic adenocarcinoma | Negative |
| Thyroid carcinoma | Negative |
| Oral squamous carcinoma | Negative |
| Ovary serous carcinoma | Negative |

Figure 15:
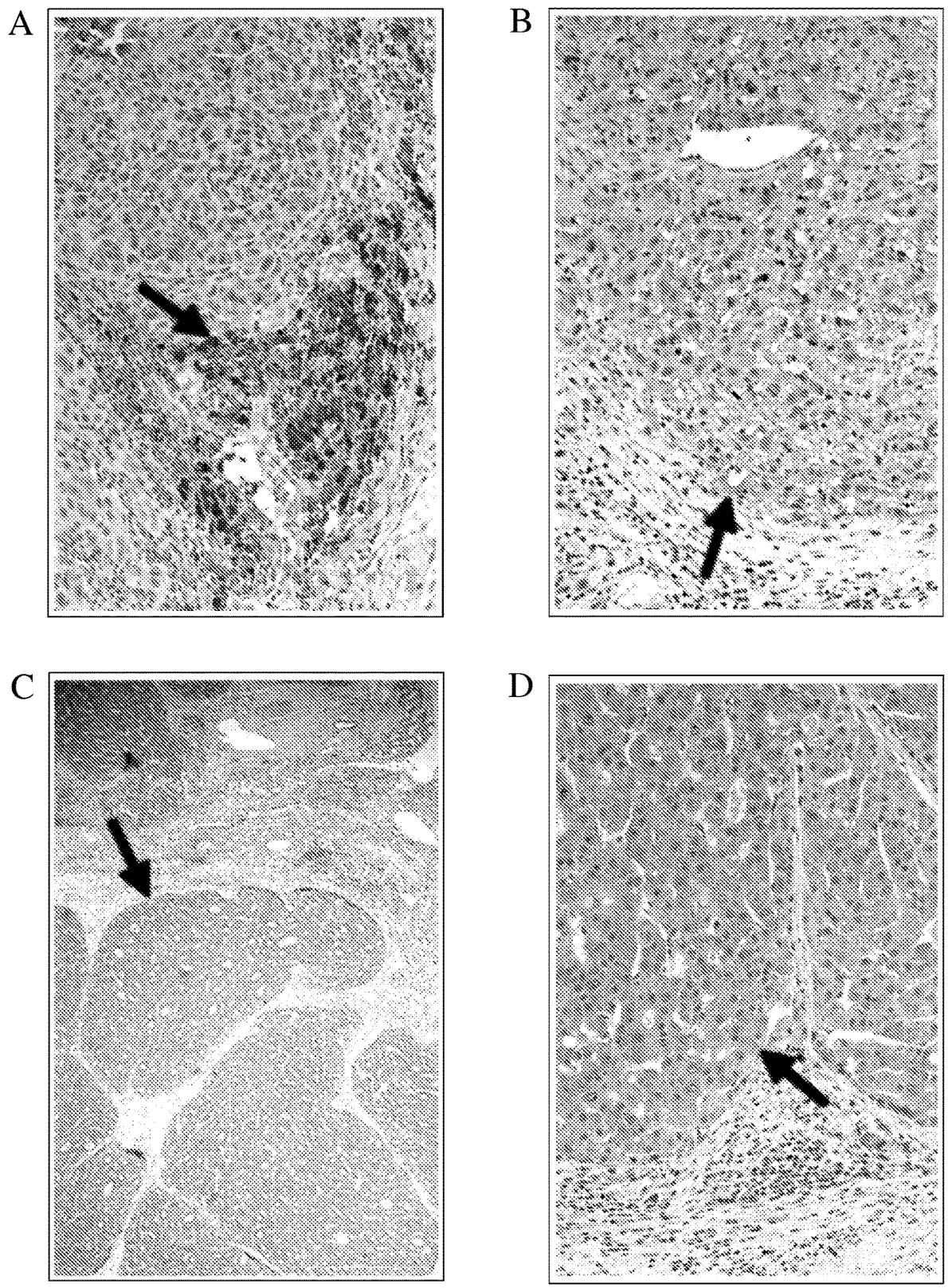
FIG. 15 shows representative images of direct IHC staining of tissue samples using a polymeric-HRP anti-ROR2 antibody conjugate. Melanoma (FIGS. 15A and 15B), hepatocellular carcinoma (FIGS. 15C and 15D), neuroendocrine tumor (FIGS. 15E and 15F), lung carcinoma (FIG. 15G), and renal clear cell carcinoma (FIG. 15H) tissue sections are illustrated. Exemplary stained areas are indicated by an arrow.
Figure 15:
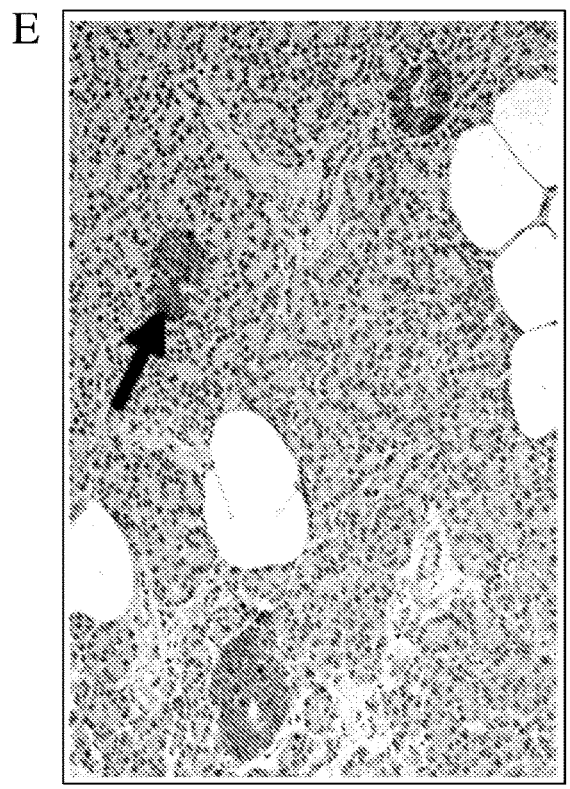
Figure 15:
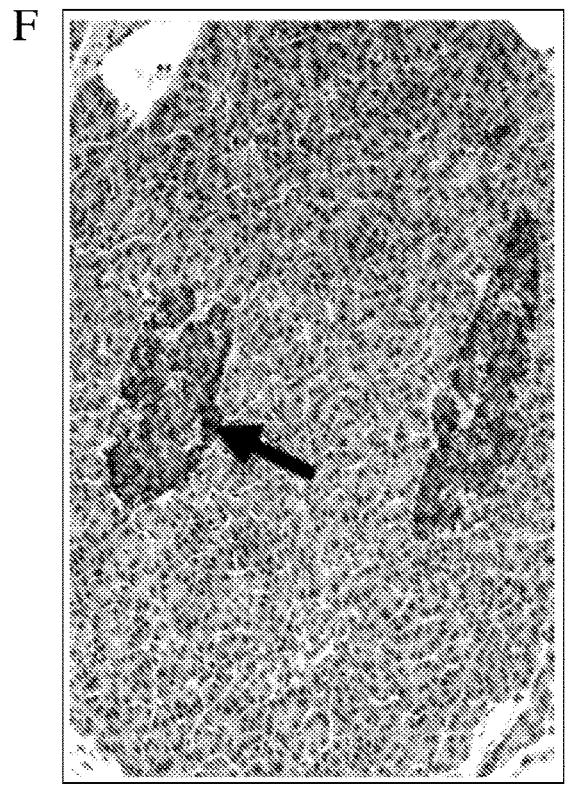
Figure 15:
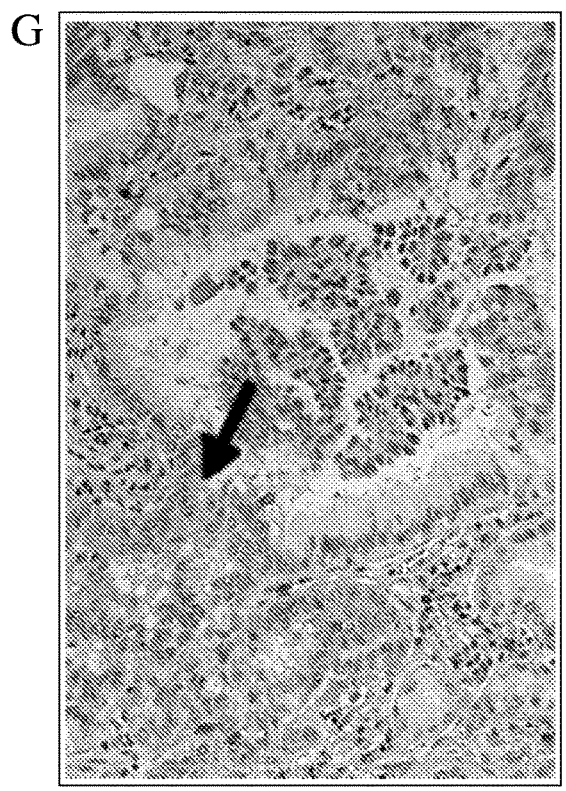
Figure 15:
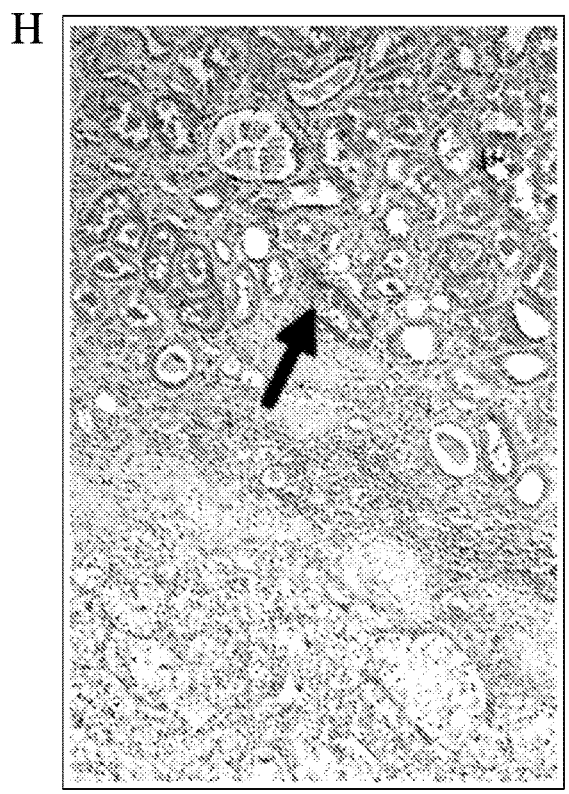

Representative images of direct IHC stained tissue are provided for the following: melanoma (FIGS. 15A and 15B), hepatocellular carcinoma (FIGS. 15C and 15D), neuroendocrine tumor (FIGS. 15E and 15F), lung carcinoma (FIG. 15G), and renal clear cell carcinoma (FIG. 15H).

We claim:

1. A method for detecting a target analyte that characterizes a disease in a tissue,
   wherein the tissue is a tissue section,
   the method comprising:
   (a) contacting the tissue comprising the target analyte with a plurality of primary polymeric-enzyme/antibody conjugates under a suitable condition to form a complex comprising the target analyte and one or more of the plurality of primary polymeric-enzyme/antibody conjugates,
   wherein each primary polymeric-enzyme/antibody conjugate comprises: (i) a plurality of polymeric-enzymes, each polymeric-enzyme comprising a plurality of enzyme molecules; and (ii) an antibody recognizing the target analyte, wherein the plurality of polymeric-enzymes are directly conjugated to the antibody, wherein each primary polymeric-enzyme/antibody conjugate has a molecular weight of about 400 kDa to about 2,000 kDa, and wherein step (a) is performed for an incubation period of 5 minutes or less;
   (b) substantially removing the primary polymeric-enzyme/antibody conjugates that do not form the complex; and
   (c) contacting the tissue with a substrate of the plurality of enzyme molecules, thereby detecting the target analyte.

2. The method of claim 1, wherein the tissue is fixed in a fixing solution comprising an aldehyde.

3. The method of claim 2, wherein the fixing solution comprises formalin.

4. The method of claim 1, wherein the tissue is a frozen tissue or a fresh tissue.

5. The method of claim 1, wherein the tissue section is selected from the group consisting of tissue sections of brain, adrenal glands, colon, small intestines, stomach, heart, liver, skin, kidney, lung, pancreas, testis, ovary, prostate, uterus, thyroid, and spleen of a mammal.

6. The method of claim 1, wherein the enzyme molecule is selected from the group consisting of: beta-D-galactosidase, glucose oxidase, horseradish peroxidase, alkaline phosphatase, beta-lactamase, glucose-6-phosphate dehydrogenase, urease, micase, superoxide dismutase, luciferase, pyruvate kinase, lactate dehydrogenase, galactose oxidase, acetylcholine-sterase, enterokinase, tyrosinase, and xanthine oxidase.

7. The method of claim 1, wherein step (a) is performed at an incubation temperature of between about 15° C. and about 37° C.

8. The method of claim 1, wherein step (a) is performed for an incubation period of between about 3 minutes and about 5 minutes.

9. A method of treating an individual having a disease characterized by a target analyte, the method comprising:
   (a) detecting the presence of the target analyte using a plurality of primary polymeric-enzyme/antibody conjugates according to the method of claim 1, and
   (b) administering an effective amount of an agent that targets the target analyte.

10. The method of claim 9, wherein the agent is a therapeutic antibody.

11. The method of claim 10, wherein the antibody that specifically binds the target analyte and the therapeutic antibody are the same.

12. The method of claim 1, wherein the number of enzyme molecules of one of the plurality of polymeric-enzymes is at least 5 enzyme molecules and less than 15 enzyme molecules.

13. The method of claim 1, wherein the number of enzyme molecules of one of the plurality of polymeric-enzymes is at least 10 enzyme molecules and less than 25 enzyme molecules.

14. The method of claim 1, wherein the number of enzyme molecules of one of the plurality of polymeric-enzymes is at least 25 enzyme molecules and less than 50 enzyme molecules.

15. The method of claim 8, wherein the tissue section is about 1.5 µm to about 5.5 µm thick.

16. The method of claim 1, wherein step (a) is performed at an incubation temperature of between about 15° C. and about 25° C.

17. The method of claim 9, wherein step (a) is performed for an incubation period of between about 3 minutes and about 5 minutes.

18. The method of claim 17, wherein step (a) is performed at an incubation temperature of between about 15° C. and about 25° C.

19. The method of claim 1, wherein the target analyte is expressed at a copy number of about $1 \times 10^3$ to $1 \times 10^4$ per cell.

* * * * *